(12) United States Patent
Liu et al.

(10) Patent No.: US 10,590,145 B2
(45) Date of Patent: Mar. 17, 2020

(54) TETRAHYDROTHIOPYRANOPYRIMIDINE DERIVATIVES AS ANTI-HIV AGENT

(71) Applicant: SHANDONG UNIVERSITY, Jinan (CN)

(72) Inventors: Xinyong Liu, Jinan (CN); Heng Zhang, Jinan (CN); Peng Zhan, Jinan (CN); Zhongxia Zhou, Jinan (CN); Dongwei Kang, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 284 days.

(21) Appl. No.: 15/735,135

(22) PCT Filed: Jul. 12, 2016

(86) PCT No.: PCT/CN2016/089710
§ 371 (c)(1),
(2) Date: Dec. 8, 2017

(87) PCT Pub. No.: WO2018/000450
PCT Pub. Date: Jan. 4, 2018

(65) Prior Publication Data
US 2020/0031844 A1    Jan. 30, 2020

(30) Foreign Application Priority Data

Jun. 27, 2016 (CN) .......................... 2016 1 04883101

(51) Int. Cl.
*C07D 495/06* (2006.01)
*A61K 31/519* (2006.01)
*C07D 495/04* (2006.01)
*A61P 31/18* (2006.01)

(52) U.S. Cl.
CPC ............ *C07D 495/04* (2013.01); *A61P 31/18* (2018.01)

(58) Field of Classification Search
CPC ........................... C07D 495/06; A61K 31/519
USPC .......................................... 544/253; 514/258
See application file for complete search history.

(56) References Cited

U.S. PATENT DOCUMENTS 8,809,343 B2 *  8/2014  Chen ................... C07D 239/47
                                                      514/258.1

* cited by examiner

*Primary Examiner* — Charanjit Aulakh
(74) *Attorney, Agent, or Firm* — CBM Patent Consulting, LLC

(57) ABSTRACT

The invention relates the tetrahydrothiopyranopyrimidine derivatives, the preparation, and the use thereof. The invention contained tetrahydrothiopyranopyrimidine derivatives, and pharmaceutical acceptable salt and prodrug with the formula I or II. Also described here are preparation of tetrahydrothiopyranopyrimidine derivatives, pharmaceutical compositions comprising these compounds as therapy and prevention for HIV.

9 Claims, No Drawings

TETRAHYDROTHIOPYRANOPYRIMIDINE DERIVATIVES AS ANTI-HIV AGENT

This application is the U.S. national phase of International Application No. PCT/CN2016/089710 filed on 12 Jul. 2016 which designated the U.S. and claims priority to Chinese Application No. CN2016104883101 filed on 27 Jun. 2016, the entire contents of each of which are hereby incorporated by reference.

FIELD OF THE INVENTION

This invention concerns tetrahydrothiopyranopyrimidine derivatives, pharmaceutically acceptable addition salts or prodrugs having HIV replication inhibiting properties. Also described herein are the preparation of these derivatives and pharmaceutical compositions comprising them.

BACKGROUND OF THE INVENTION

Acquired immune deficiency syndrome (AIDS), caused by infection of human immunodeficiency virus (HIV), results in more than 2 million human death every year and is still a global social concern nowadays. Although more than 30 years has pasted since the first report of AIDS, the cures or vaccines are remained elusive. To date, an arsenal of 28 new chemical entity drugs have been approved by FDA, but none of them could eliminate the virus completely. Although the highly active antiretroviral therapies (HAART) could significantly reduce the morbidity and mortality of AIDS, the severe side effects and drug resistance along with the long-term use of approved drugs result in the suspending of treatment. So, there is an urgent the development of novel inhibitors with improved tolerability and resistance profiles.

Reverse transcriptase (RT) plays essential roles in the life cycle of HIV-1 virus and it is responsible for reverse transcription of viral single-stranded RNA into double stranded viral DNA. For the well solved 3D structure and a well-known action mechanism, RT has been regarded as an attractive target for years. According to the action mechanism, RT inhibitors are divided into two classes: nucleoside reverse transcriptase inhibitors (NRTIs) and non-nucleoside reverse transcriptase inhibitors (NNRTIs), while NNRTIs attract comprehensive attentions for their high potency and low toxicity. However, for the error prone of replication, drug-resistant mutants with reduced susceptibility to NNRTIs have emerged rapidly and lead to the failure of clinical drugs, so considerable efforts have been applied towards finding novel inhibitors with anti-resistance profiles.

Diarylpyrimidine (DAPY) derivatives are second generation NNRTIs with high potency, low toxicity and promising anti-resistance profiles, with two compounds (Etravirine and Rilpivirine) have been marketed. But for the intrinsic specificity, DAPY derivatives demonstrate low solubility, which lead to poor bioavailability. Thus, it is necessary to discover new inhibitors with potent anti-drug resistance profiles, and favorable oral bioavailability.

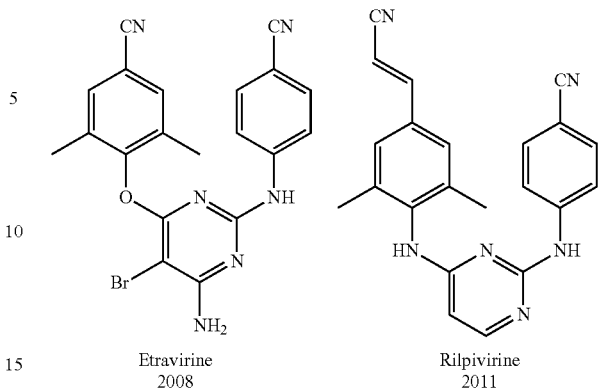

Etravirine 2008

Rilpivirine 2011

SUMMARY OF THE INVENTION

Considering the deficiencies of the prior art, the present invention provides a series of tetrahydrothiopyranopyrimidine derivatives and their preparing thereof, as well as their applications as anti-HIV inhibitors.

1. Tetrahydrothiopyranopyrimidine Derivatives

The invention provided a series of tetrahydrothiopyranopyrimidine derivatives of formula I or II

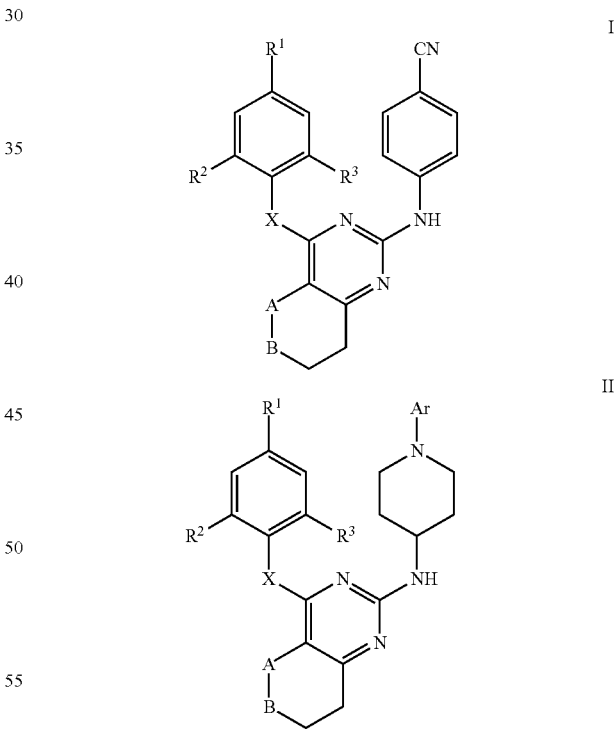

the pharmaceutically acceptable addition salts or prodrugs, wherein

A is $S(=O)_n$ or $CH_2$; B is $S(=O)$, or $CH_2$, while either A or B is $S(=O)_n$; n=0, 1 or 2;

X is O or NH;

$R^1$, $R^2$ and $R^3$ are each independently selected from hydrogen, halo, cyano, trifluoromethyl, amino, hydroxyl, cyanovinyl, cyanoethyl, cyclopropyl, $C_{1-6}$alkyl, $C_{1-6}$alkyloxyl or $C_{2-6}$alkenyl;

Ar is an optionally substituted mono- or polycyclic aromatic ring, an optionally substituted mono- or polycyclic heteroaromatic ring, an optionally substituted mono- or polycyclic saturated ring, an optionally substituted mono- or polycyclic saturated heterocyclic ring;

Preferably, $R^1$, $R^3$ are methyl, $R^2$ is selected from cyano, methyl or cyanovinyl;

Ar is selected from formula (a) or (b) below:

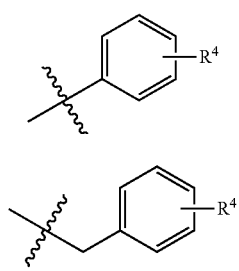

wherein $R^4$ is selected from hydrogen, cyano, methyl, nitro, amino, $COR^5$, $COOR^5$, $CONH_2$, $CONHR^5$, $SO_2R^5$, $SO_2NH_2$, $SO_2NHR^5$, $NHR^5$, $NHCOR^5$ or $NHSO_2R^5$;

$R^5$ is selected from among $C_{1-10}$alkyl, $C_{1-10}$cyclicalkyl, $C_{1-10}$haloalkyl, $C_{1-10}$alkenyl, or $C_{1-10}$aromatic alkyl.

Preferably, $R^5$ is methyl or acetyl.

The term halo defines fluoro, chloro, bromo and ido;

The term "pharmaceutical acceptable addition salt" is a medical term, which refers to salts which could administrate to an individual or animal and don't cause undesirable toxic, irritation or allergic reactions, with reasonable profit/risk characters at the same time; It is usually water or oil soluble or dispersible, and used as specific purpose. The term "pharmaceutical acceptable addition salt" including pharmaceutical acceptable acid addition salts or base addition salts, which can be effectively used as specific purpose and compatible with compounds described herein. The pharmaceutical acceptable addition salts are reviewed in S. M. Birge et al. *J. Pharm. Sci.*, 1977, 66, 1-19.

The term "prodrug" refers to a drug precursor that is capable of providing, either directly or indirectly, a compound disclosed herein or a pharmaceutically active metabolite or residue thereof.

Preferably, compounds described here with structures of formula (IA-1), (IA-2), (IB-1), (IB-2), (IIA-1), (IIA-2), (IIB-1), (IIB-2), (IIC-1), (IIC-2), (IID-1), and (IID-2):

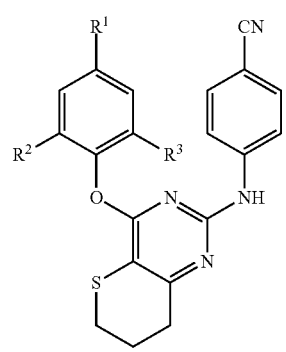
IA-1

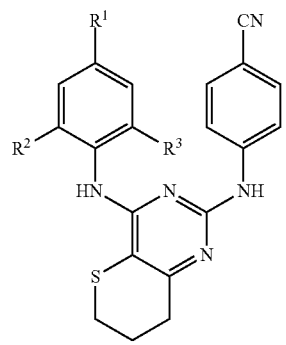
IA-2

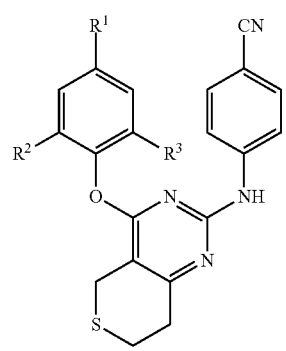
IB-1

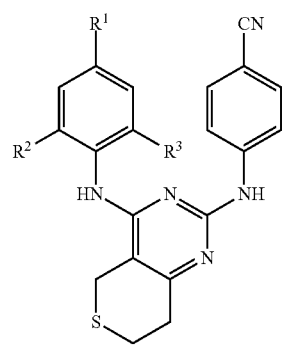
IB-2

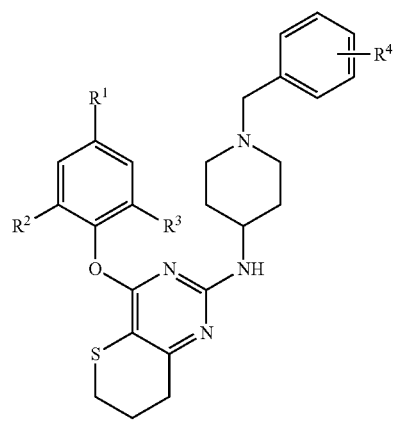
IIA-1

IIA-2
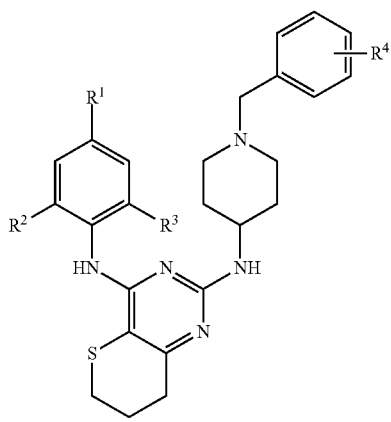
IIB-1
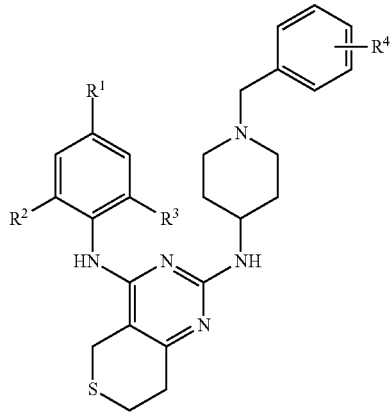
IIB-2
IIC-1
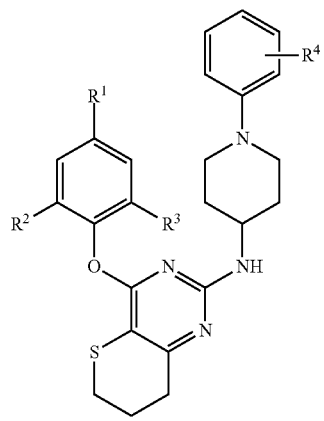
IIC-2
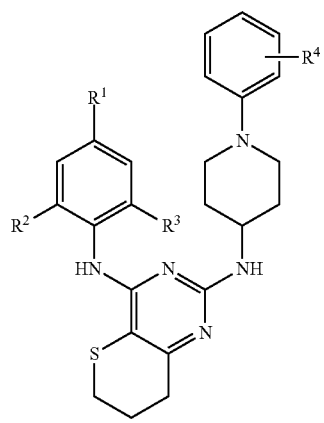
IID-1
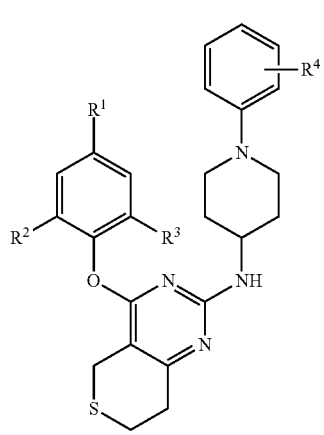

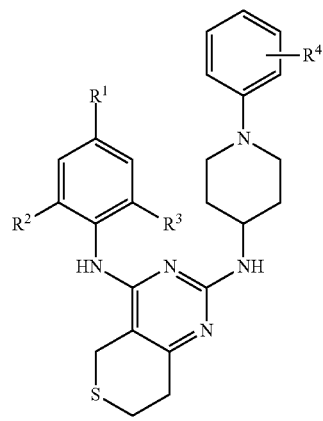

IID-2 wherein, $R^1$, $R^2$, $R^3$ independently are hydrogen, halo, cyano, trifluoromethyl, amino, hydroxyl, $C_{1-6}$alkyl, $C_{1-6}$alkyloxy, $C_{2-6}$alkenyl, cyanovinyl, cyanoethyl or cyclopropyl; $R^4$ is selected from among hydrogen, cyano, methyl, $COR^5$, $COOR^5$, $CONH_2$, $CONHR^5$, $SO_2R^5$, $SO_2NH_2$, $SO_2NHR^5$, nitro, amino, $NHR^5$, $NHCOR^5$ or $NHSO_2R^5$; $R^5$ is selected from among $C_{1-10}$alkyl, $C_{1-10}$cyclicalkyl, $C_{1-10}$haloalkyl, $C_{1-10}$alkenyl, or $C_{1-10}$aromatic alkyl.

Preferably, tetrahydrothiopyranopyrimidine derivatives are compounds as follow:

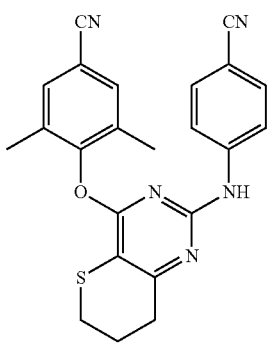

IA-1-1

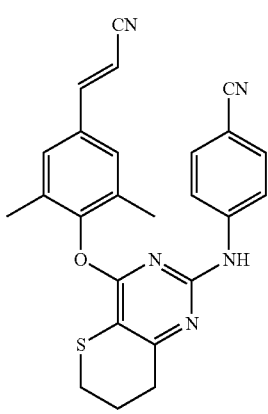

IA-1-2

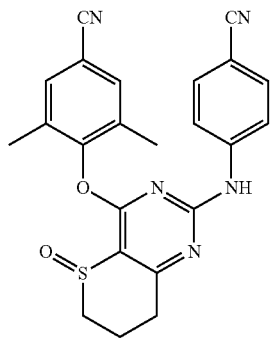

IA-1-3

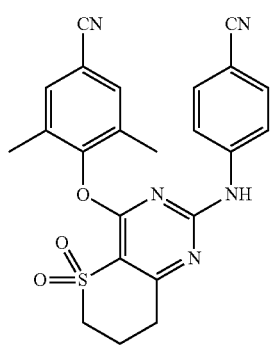

IA-1-4

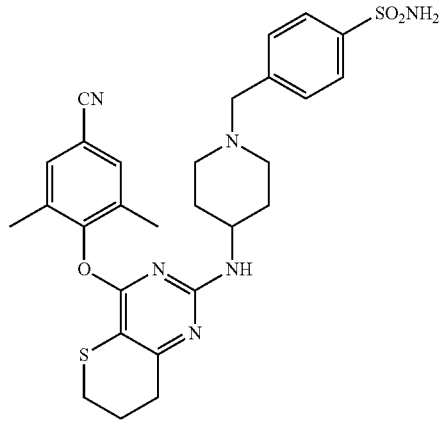

IIA-1-1

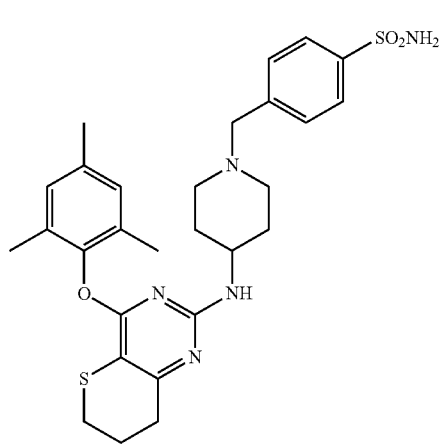

IIA-1-2

IIA-1-3
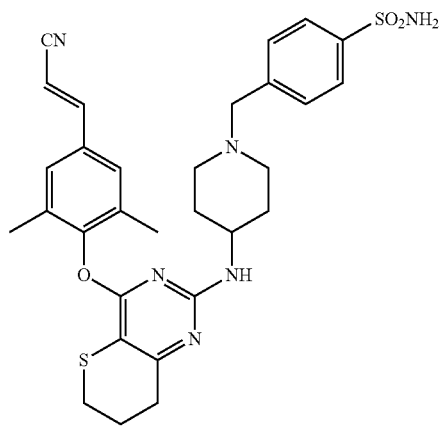
IIA-1-4
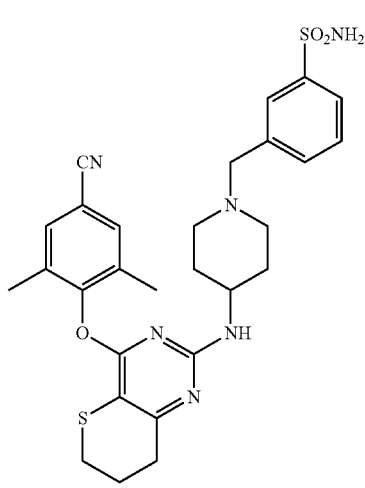
IIA-1-5
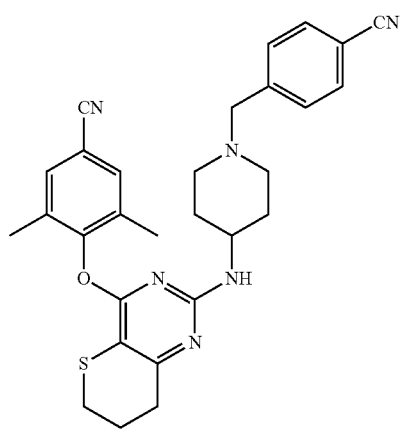
IIA-1-6
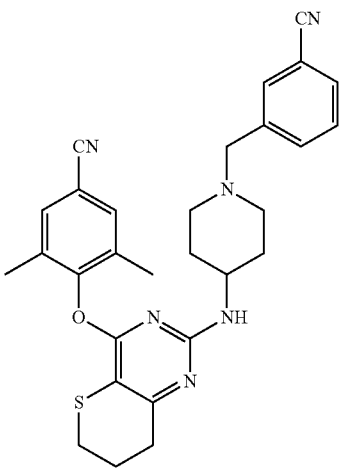
IIA-1-7
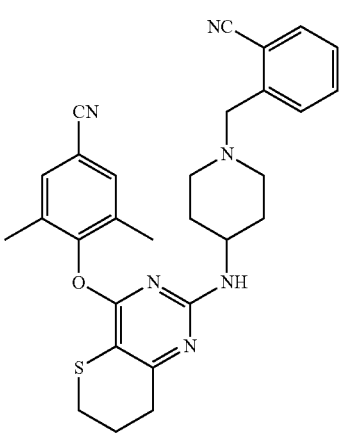
IIA-1-8
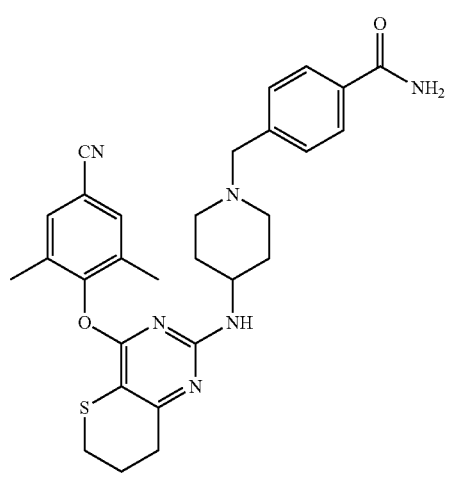

-continued
IIA-1-9
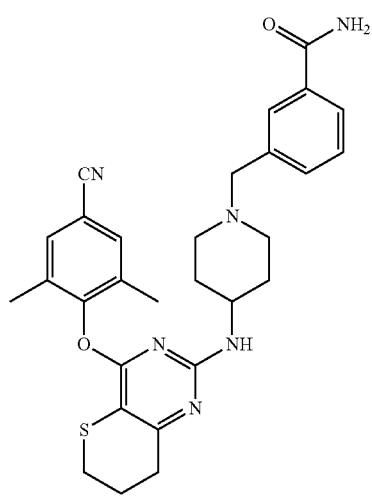
IIA-1-10
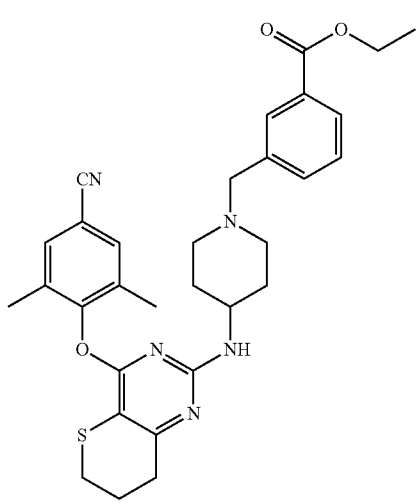
IIA-1-11
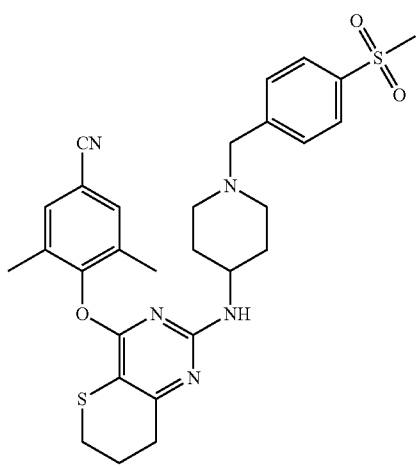
-continued
IIA-1-12
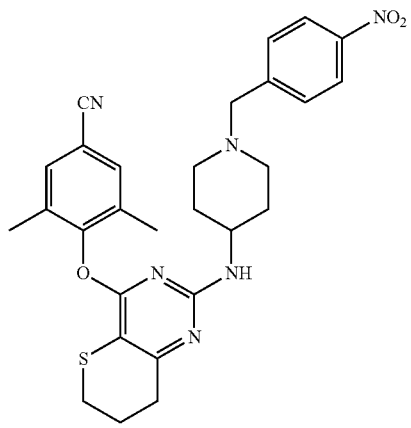
IIA-1-13
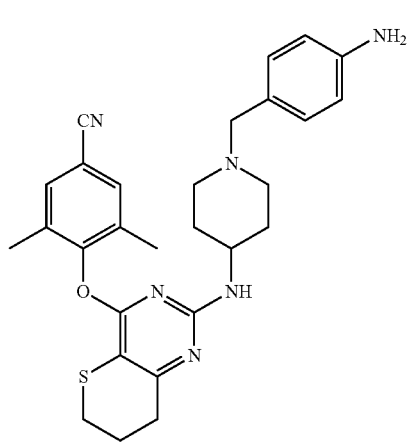
IIA-1-14
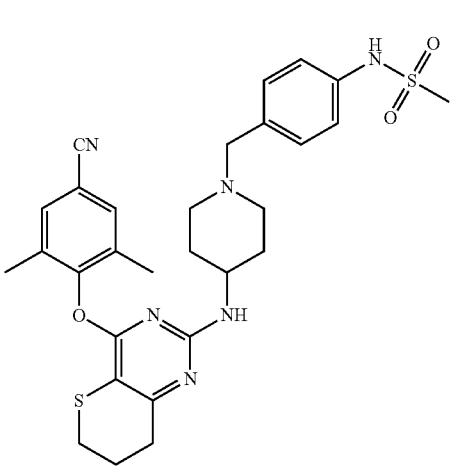

-continued

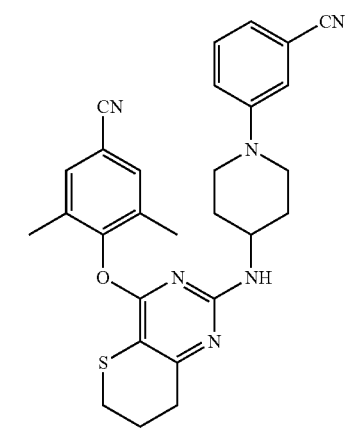
IIC-1-1

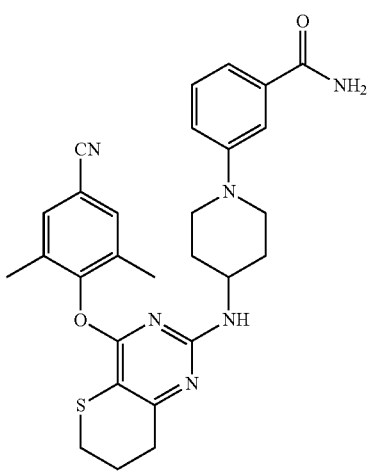
IIC-1-2

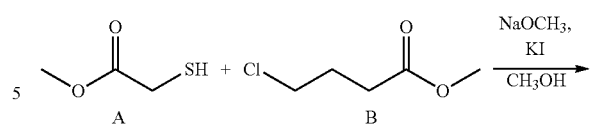

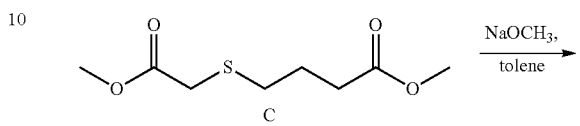

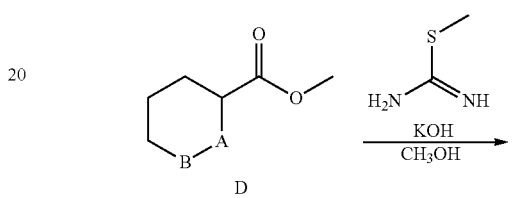

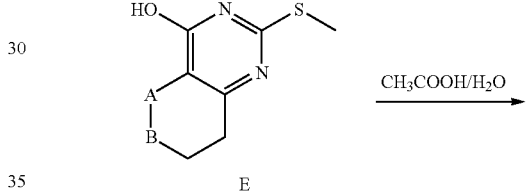

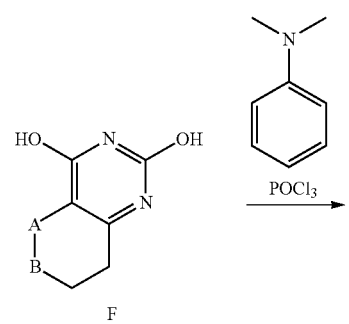

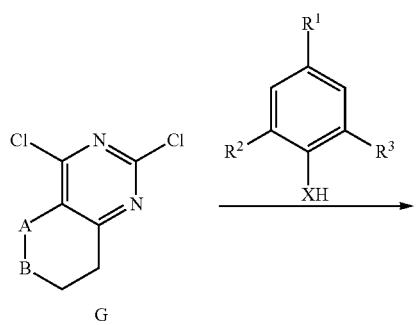

2. Preparation of Tetrahydrothiopyranopyrimidine Derivatives

The tetrahydrothiopyranopyrimidine derivatives can be prepared as follows:

The preparation of tetrahydrothiopyranopyrimidine ring (G) was synthesized as described by Taiji Goto et al. *Biorg. Med. Chem. Lett.* 2014, 24, 893-899, Zhu, Wufu et al. *Biorg. Med. Chem.* 2014, 22, 6746-6754. A substitute reaction of methyl thioglycolate (A) and methyl 4-chlorobutanoate (B) gave methyl 4-((2-methoxy-2-oxoethyl)thio)butanoate (C), then a successive Dieckmann condensation reaction provided ketoester (D). The pyrimidine ring was constructed by a cyclization reaction of ketoester D with S-methylisothiourea and the resultant E was treated with acetic acid/$H_2O$ to provide 2,4-dihydroxypyrimidine F. After conversion of the hydroxyl groups to chlorine atoms using phosphoryl chloride, 2,4,6-trisubstituted phenol/aniline was introduced selectively to the 4-position of the pyrimidine ring to afford H. The 4-substituted pyrimidine H can react with 4-aminobenzonitrile to give compounds IA and IB, and further Oxidation of IA afford corresponding compounds. The 4-substituted pyrimidine H can also be substituted by 1-Boc-4-aminopiperidine. After deprotection, H reacted with corresponding substituted benzyl chloride/bromide to prepare IIA-IIB. Besides, the 4-substituted pyrimidine H can directly react with 1-substituted-4-aminopiperidine to synthesize IIC-IID.

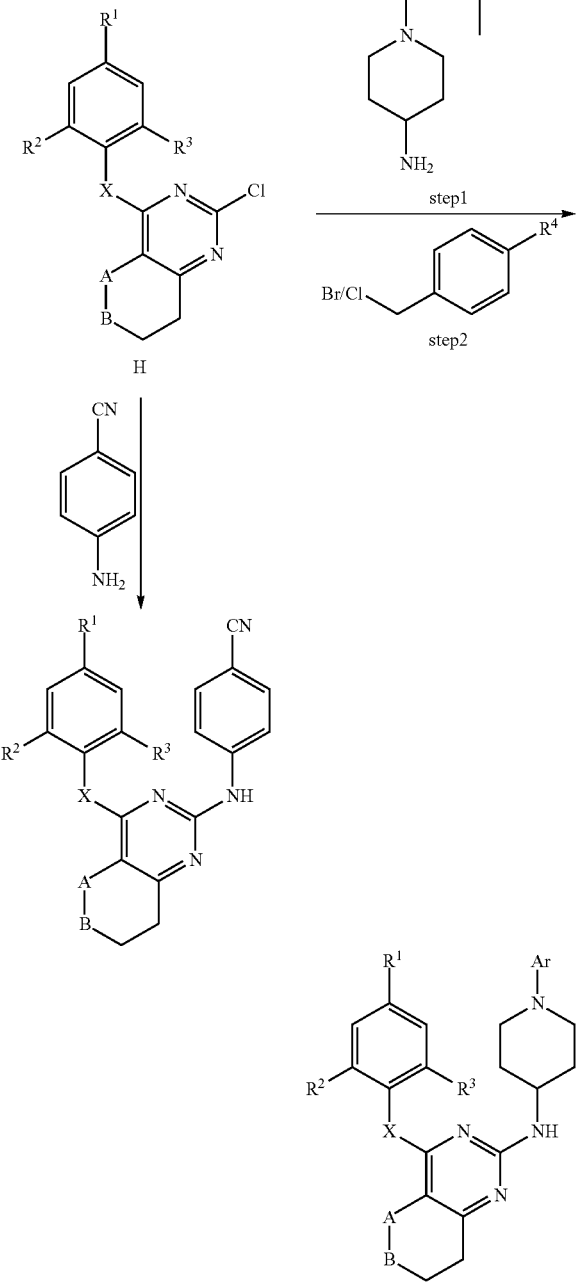

luorobenzene, 2-(chloromethyl)benzonitrile, 3-(chloromethyl)benzonitrile, 4-(chloromethyl)benzonitrile, 1-(cholomethyl)-2-nitrobenzene, 1-(chloromethyl)-3-nitrobenzene, 1-(chloromethyl)-4-nitrobenzene, 1-(chloromethyl)-2-methoxybenzene, 1-(chloromethyl)-3-methoxybenzene, 1-(chloromethyl)-4-methoxybenzene, 1-(bromomethyl)-4-(methylsulfonyl)benzene, 4-(bromomethyl)benzenesulfonamide, 3-(bromomethyl)benzenesulfonamide, 2-(bromomethyl)benzamide, N-(4-(bromomethyl)phenyl)formamide, ethyl 4-(bromomethyl)benzoate, 4-(bromomethyl)benzamide, 3-(bromomethyl)benzamide, N-(4-(bromomethyl)phenyl)methanesulfonamide.

While the $R^1$, $R^2$, $R^3$, A, B, X, Ar are the same as the groups of above formula I and II.

3. Activity Against Wide-Type and Mutant HIV-1 and Use Thereof

Selected compounds are tested for their anti-HIV-1 activity in MT-4 cell cultures infected with the wide-type HIV-1 (strain IIIB), L100I, K103N, Y181C, Y188L, E138K mutant strains, and the double RT mutant RES056 (K103N/Y181C) and F227L/V106A strains. As indicated from the results that the newly invented tetrahydrothiopyranopyrimidine derivatives with novel scaffold are very potent NNRTIs with excellent activity against both wide-type and mutant strains. So, they can serve as lead compounds for further development.

Also described here are tetrahydrothiopyranopyrimidine derivatives used as HIV-1 NNRTIs, furthermore, these HIV-1 inhibitors will be used as anti-AIDS drugs.

Also described here are pharmaceutical compositions comprising tetrahydrothiopyranopyrimidine derivatives, and with one or more kind of pharmaceutically acceptable carrier or excipient.

Also described here are novel tetrahydrothiopyranopyrimidine derivatives, the method for preparing of these compounds, and their first application in the treatment of HIV-1 thereof. Confirmed by experiments, the invented compounds are highly potent anti-HIV agents with excellent activity, which can be used as anti-AIDS drugs.

EXAMPLES

Selected examples are listed as follows, the invention includes these compounds disclosed herein but not confined to them.

Example 1: Preparation of Intermediate 7

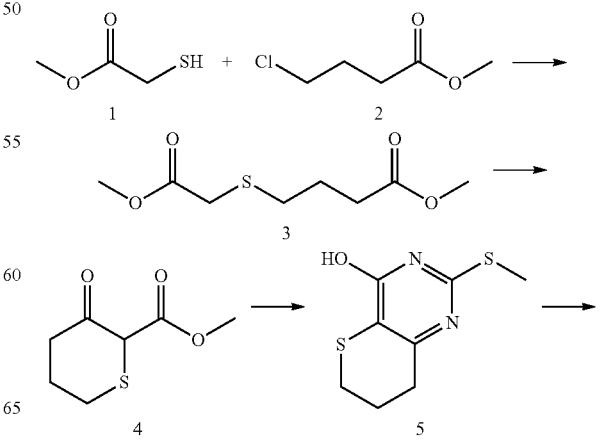

Wherein, the 2,4,6-trisubstituted phenol/aniline is selected from 2,4,6-trimethylphenol, 4-hydroxy-3,5-dimethylbenzonitrile, (E)-3-(4-hydroxy-3,5-dimethylphenyl)acrylonitrile, 2,4,6-trimethylaniline, 4-amino-3,5-dimethylbenzonitrile, and (E)-3-(4-amino-3,5-dimethylphenyl)acrylonitrile.

Wherein, the substituted benzyl chloride/bromide is selected from 1-chloro-2-(chloromethyl)benzene, 1-chloro-3-(chloromethyl)benzene, 1-chloro-4-(chloromethyl)benzene, 1-bromo-2-(bromomethyl)benzene, 1-bromo-3-(bromomethyl)benzene, 1-bromo-4-(bromomethyl)benzene, 1-(chloromethyl)-2-fluorobenzene, 1-(chloromethyl)-3-fluorobenzene, 1-(chloromethyl)-4-fluorobenzene, 1-(bromomethyl)-2,4-difluorobenzene, 1-(bromomethyl)-3,4-dif-

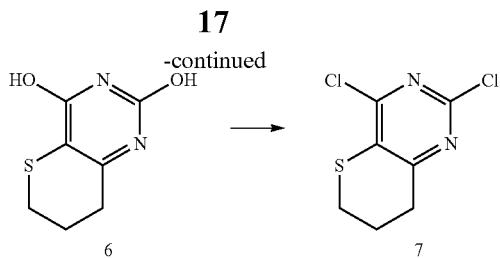

Step A: methyl 4-((2-methoxy-2-oxoethyl)thio)butanoate (3)

To a solution of sodium methoxide (2.75 g, 51 mmol) in MeOH (30 mL) was added methyl-2-mercaptoacetate (1, 7.85 mL, 87.8 mmol) and the reaction mixture was stirred at room temperature for 0.5 h. Potassium iodide (50 mg) and methyl-4-chlorobutanoate (2, 6.2 mL, 101 mmol) were added to the reaction mixture, which was stirred at 65° C. for 20 h. After cooling, the reaction mixture was filtered and the resultant filtrate was concentrated under reduced pressure. $CH_2Cl_2$ (100 mL) was added to the residue and the mixture was extracted with $H_2O$ (3×20 mL). The combined organic layer was washed with brine, dried over $Na_2SO_4$, and concentrated in vacuo to give methyl-4-((2-methoxy-2-oxoethyl)thio)butanoate (3) as a pale yellow oil. This compound was used for the next reaction without further purification. $^1$H NMR (600 MHz, $CDCl_3$) δ: 3.75 (s, 3H), 3.66 (s, 3H), 3.21 (s, 2H), 2.77 (t, J=7.2 Hz, 2H), 2.66 (t, J=7.2 Hz, 2H), 1.93 (p, J=7.2 Hz, 2H). ESI-MS: m/z 207.3 (M+1)$^+$, 224.4 (M+18)$^+$. $C_8H_{14}O_4S$ (206.06).

Step B: methyl 3-oxotetrahydro-2H-thiopyran-2-carboxylate (4)

To a solution 3 (5.00 g, 24.3 mmol) in anhydrous toluene (40 mL) was added sodium methoxide (1.43 g, 26.5 mmol) and heated at 105° C. for 3 h. After cooling to room temperature, 12N HCl (5 mL) was added. The mixture was extracted with ethyl acetate (3×30 mL). The combined organic layers were washed with brine, then dried over $Na_2SO_4$, the filtrate was concentrated under reduced pressure and purified by silica-gel column chromatography to afford methyl-3-oxotetrahydro-2H-thiopyran-2-carboxylate (4) as a yellow oil (1.93 g, 45.8%). $^1$H NMR ($CDCl_3$) δ: 12.18 (1H, s), 2.79-2.83 (2H, m), 2.42 (2H, t, J=6.6 Hz), 2.10-2.17 (2H, m). ESI-MS: m/z 175.3 (M+1)$^+$, 192.5 (M+18)$^+$. $C_7H_{10}O_3S$ (174.04).

Step C: 2-(methylthio)-7,8-dihydro-6H-thiopyrano[3,2-d]pyrimidin-4-ol (5)

To a solution of KOH (0.57 g, 10.76 mmol) in MeOH (30 mL) were added 4 (1.25 g, 7.17 mmol) and S-methylisothiourea sulfate (1.00 g, 3.58 mmol). After stirring at room temperature for 16 h, the reaction mixture was poured into ice water (40 mL) and AcOH (2.0 mL) was added. The resultant precipitate was collected by filtration and washed with $H_2O$ to give 2-(methylthio)-7,8-dihydro-6H-thiopyrano[3,2-d] pyrimidin-4-ol (5) as a white solid. This compound was used for the next reaction without further purification. mp 234-236° C. $^1$H NMR (400 MHz, DMSO-$d_6$) δ: 12.70 (s, 1H), 2.94-2.84 (m, 2H), 2.61 (t, J=6.3 Hz, 2H), 2.45 (s, 3H), 2.08-1.95 (m, 2H). ESI-MS: m/z 215.4 (M+1)$^+$, 237.3 (M+23)$^+$. $C_8H_{10}N_2OS_2$ (214.02).

Step D: 7,8-dihydro-6H-thiopyrano[3,2-d]pyrimidine-2,4-diol (6)

To a solution of 2-(methylthio)-7,8-dihydro-6H-thiopyrano[3,2-d]pyrimidin-4-ol 5 (1.05 g) in $H_2O$ (10 mL) was added acetic acid (20 mL) and the reaction mixture was stirred at 110° C. for 3 days. After cooling, the resultant precipitate was collected by filtration to give 7,8-dihydro-6H-thiopyrano[3,2-d]pyrimidine-2,4-diol (6, 0.5 g, 37.7% two steps) as a colorless crystal. mp>300° C. $^1$H NMR (400 MHz, DMSO-$d_6$) δ: 11.17 (s, 1H), 10.82 (s, 1H), 2.84 (d, J=6.0 Hz, 2H), 2.43 (t, J=6.3 Hz, 2H), 2.04-1.91 (m, 2H). ESI-MS: m/z 185.0 (M+1)$^+$, 207.2 (M+23)$^+$. $C_7H_8N_2O_2S$ (184.03).

Step E: 2,4-dichloro-7,8-dihydro-6H-thiopyrano[3,2-d]pyrimidine (7)

A solution of 6 (0.42 g, 2.3 mmol) and N,N-dimethylaniline (70 μL) in phosphoryl chloride (2.0 mL) was stirred at 90° C. for 18 h. After cooling, the reaction mixture was poured into ice water (50 mL) and the mixture was extracted with $CH_2Cl_2$ (30 mL×3). The combined organic layer was washed with brine, dried over $Na_2SO_4$, and concentrated in vacuo. The residue was chromatographed to give 2,4-dichloro-7,8-dihydro-6H-thiopyrano[3,2-d]pyrimidine (7) as a pale gray solid (0.35 g, 69.4%). mp 105-108° C. $^1$H NMR ($CDCl_3$) δ: 3.09-3.13 (2H, m), 2.99 (2H, t, J=6.3 Hz), 2.21-2.28 (2H, m). ESI-MS: m/z 221.3 (M+1)$^+$. $C_7H_6Cl_2N_2S$ (219.96).

Example 2: Preparation of Intermediate 8

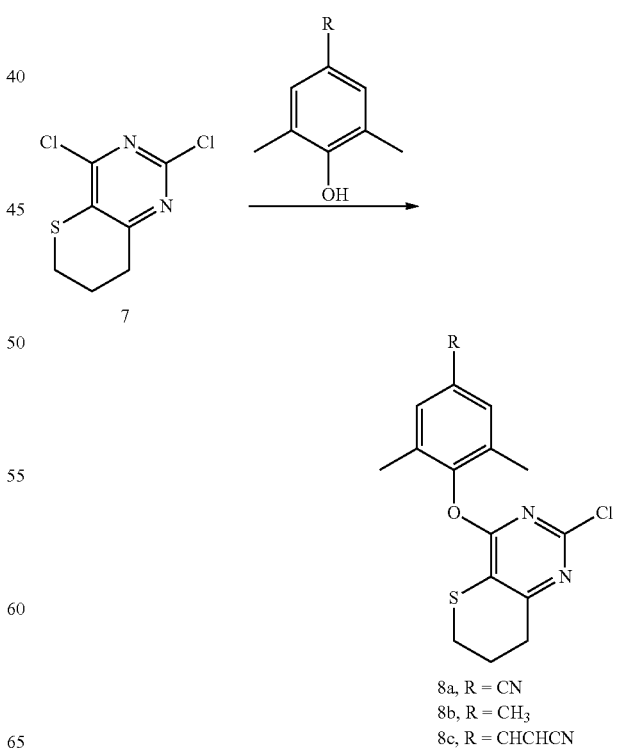

8a, R = CN
8b, R = $CH_3$
8c, R = CHCHCN

4-((2-chloro-7,8-dihydro-6H-thiopyrano[3,2-d]pyrimidin-4-yl)oxy)-3,5-dimethylbenzonitrile (8a)

To a solution of 7 (0.5 g, 2.26 mmol) in DMF were added $K_2CO_3$ (0.38 g, 2.71 mmol) and 2,4,6-trimethylphenol (0.40 g, 2.71 mmol), and stirred at room temperature overnight, the mixture was filtered and evaporated under reduce pressure. $CH_2Cl_2$ was added to the residue and the mixture was extracted with $H_2O$. The organic layer was then washed with brine, dried over $Na_2SO_4$, concentrated under reduced pressure and recrystallized from ethyl acetate and petroleum ether to give 4-((2-chloro-7,8-dihydro-6H-thiopyrano[3,2-d]pyrimidin-4-yl)oxy)-3,5-dimethylbenzonitrile (8a, 0.54 g, 72.5%) as a pale grey solid. mp 254-255° C. $^1$H NMR (400 MHz, DMSO-$d_6$) δ: 7.73 (s, 2H), 3.16 (d, J=5.6 Hz, 2H), 2.92 (t, J=6.2 Hz, 2H), 2.23-2.13 (m, 2H), 2.07 (s, 6H). ESI-MS: m/z 332.4 (M+1)$^+$. $C_{16}H_{14}ClN_3OS$ (331.05).

2-chloro-4-(mesityloxy)-7,8-dihydro-6H-thiopyrano[3,2-d]pyrimidine (8b)

Synthesized in a similar procedure with intermediate 7 using 2,4,6-trimethylphenol as starting material.

Yield 72.5%, mp 176-179° C. $^1$H NMR (400 MHz, DMSO-$d_6$) δ: 7.05 (s, 2H), 3.04-2.93 (m, 2H), 2.66 (t, J=6.1 Hz, 2H), 2.24 (s, 3H), 2.09 (dt, J=12.1, 6.1 Hz, 2H), 1.98 (s, 6H). ESI-MS: m/z 321.4 (M+1)$^+$. $C_{16}H_{17}ClN_2OS$ (320.08).

(E)-3-(4-((2-chloro-7,8-dihydro-6H-thiopyrano[3,2-d]pyrimidin-4-yl)oxy)-3,5-dimethylphenyl)acrylonitrile (8c)

Synthesized in a similar procedure with intermediate 7 using (E)-3-(4-hydroxy-3,5-dimethylphenyl)acrylonitrile as starting material.

Yield 86.1%, mp 240-242° C. $^1$H NMR (400 MHz, CDCl$_3$) δ: 7.34 (d, J=16.7 Hz, 1H), 7.19 (s, 2H), 5.82 (d, J=16.6 Hz, 1H), 3.17-3.05 (m, 2H), 2.97 (t, J=6.3 Hz, 2H), 2.30 (p, J=6.2 Hz, 2H), 2.13 (s, 6H). ESI-MS: m/z 358.3 (M+1)$^+$. $C_{18}H_{16}ClN_3OS$ (357.07).

Example 3: Preparation of IA-1

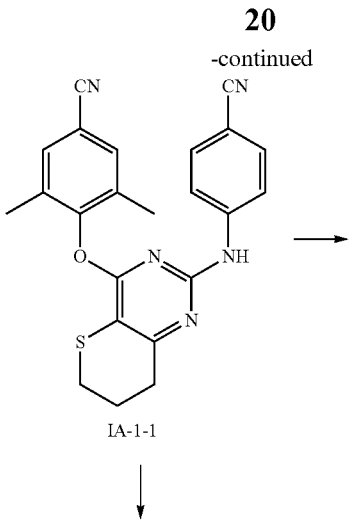

IA-1-1

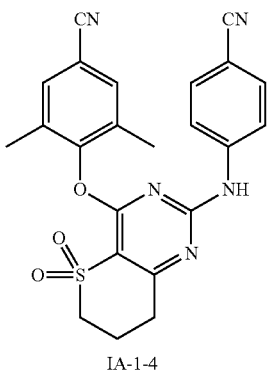

IA-1-4

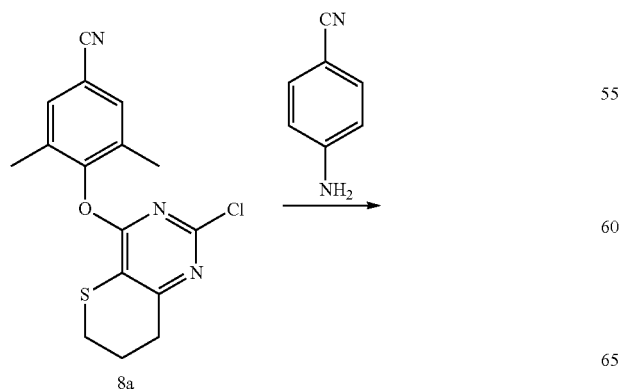

8a

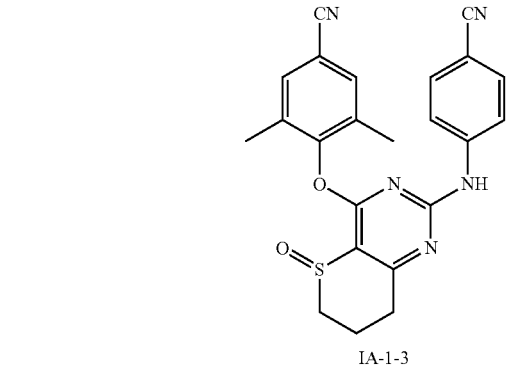

IA-1-3

4-((2-((4-cyanophenyl)amino)-7,8-dihydro-6H-thiopyrano[3,2-d]pyrimidin-4-yl)oxy)-3,5-dimethylbenzonitrile (IA-1-1)

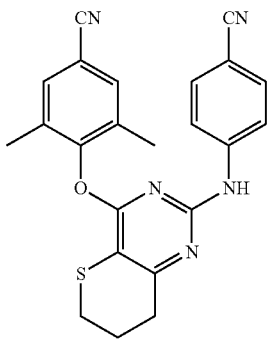

IA-1-1

To a solution of 8a (0.50 g, 1.5 mmol) and 4-aminobenzonitrile (0.36 g, 3 mmol) in 1,4-dioxane ((20 mL), BINAP (93 mg, 0.15 mmol) and Pd$_2$(dba)$_3$ (140 mg, 0.15 mmol) were added and stirred for 10 min; Cs$_2$CO$_3$ (0.98 g, 3 mmol) was added and the mixture was heated to 100° C. under N$_2$ atmosphere overnight. Residue was filtered and evaporated under reduced pressure. Ethyl acetate (100 mL) was added and extracted with H$_2$O (3×20 mL), organic layer was washed with brine, dried with Na$_2$SO$_4$ and concentrated under reduced pressure. The crude material was purified by column chromatography over silica gel (200-300 mesh) with MeOH/CH$_2$Cl$_2$ as an eluent to give 4-((2-((4-cyanophenyl)amino)-7,8-dihydro-6H-thiopyrano[3,2-d]pyrimidin-4-yl)oxy)-3,5-dimethylbenzonitrile (IA-1-1) as a white solid (0.48 g, 77.0%). mp 253-254° C. $^1$H NMR (400 MHz, DMSO-d$_6$) δ: 9.98 (s, 1H), 7.78 (s, 2H), 7.45 (s, 4H), 3.19-3.05 (m, 2H), 2.88 (t, J=6.2 Hz, 2H), 2.26-2.16 (m, 2H), 2.11 (s, 6H). $^{13}$C NMR (100 MHz, DMSO) δ: 163.63, 163.07, 154.68, 154.12, 145.20, 133.10, 133.02, 132.98, 119.92, 119.00, 118.05, 109.09, 104.50, 102.39, 31.74, 26.34, 22.96, 16.12. ESI-MS: m/z 414.5 (M+1)$^+$, 431.5 (M+18)$^+$. C$_{23}$H$_{19}$N$_5$OS (413.13).

(E)-4-((4-(4-(2-cyanovinyl)-2,6-dimethylphenoxy)-7,8-dihydro-6H-thiopyrano[3,2-d]pyrimidin-2-yl)amino)benzonitrile (IA-1-2)

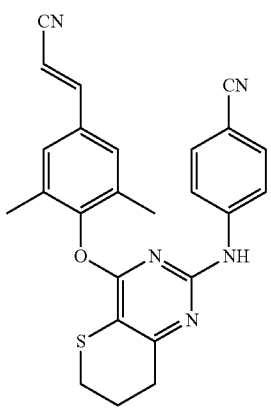

IA-1-2

Synthesized in a similar procedure with example 3 using (E)-3-(4-((2-chloro-7,8-dihydro-6H-thiopyrano[3,2-d]pyrimidin-4-yl)oxy)-3,5-dimethylphenyl)acrylonitrile as starting material.

Yield 64.3%, mp 278-280° C. $^1$H NMR (400 MHz, DMSO-d$_6$) δ: 9.95 (s, 1H), 7.68 (d, J=16.7 Hz, 1H), 7.54 (s, 2H), 7.48 (d, J=8.6 Hz, 2H), 7.39 (d, J=8.8 Hz, 2H), 6.48 (d, J=16.7 Hz, 1H), 3.19-3.06 (m, 2H), 2.87 (t, J=6.2 Hz, 2H), 2.20 (p, J=6.0 Hz, 2H), 2.08 (s, 6H). $^{13}$C NMR (100 MHz, DMSO) δ: 163.47, 163.30, 154.76, 152.47, 150.45, 145.29, 132.97, 131.93, 131.63, 128.64, 119.95, 119.33, 118.06, 104.49, 102.26, 96.93, 31.71, 26.33, 22.98, 16.40. ESI-MS: m/z 440.6 (M+1)$^+$, 457.6 (M+18)$^+$. C$_{25}$H$_{21}$N$_5$OS (439.15).

4-((2-((4-cyanophenyl)amino)-5-oxido-7,8-dihydro-6H-thiopyrano[3,2-d]pyrimidin-4-yl)oxy)-3,5-dimethylbenzonitrile (IA-1-3)

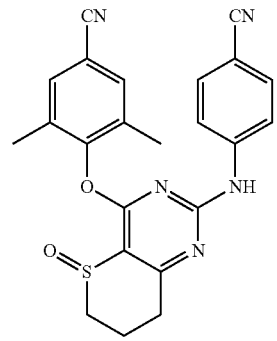

IA-1-3

Compound IA-1-1 (200 mg, 0.48 mmol) was dissolved in CH$_2$Cl$_2$ (5 mL) and cooled to −78° C., a mixture of mCPBA (107 mg, 0.57 mmol) in CH$_2$Cl$_2$ (3 mL) was added and stirred for 1 h. Residue was heated to room temperature and NaHSO$_3$ (30 mL) was added, extracted with ethyl acetate (20 mL×3). Combined organic layer and washed with brine, dried with Na$_2$SO$_4$ and concentrated under reduced pressure. Recrystallized from MeOH/CHCl$_3$ to give compound IA-1-3 (150 mg, 72.2%) as a white solid. mp 247-249° C. $^1$H NMR (400 MHz, DMSO-d$_6$) δ: 10.52 (s, 1H), 7.80 (d, J=4.6 Hz, 2H), 7.50 (s, 4H), 3.32-3.19 (m, 1H), 3.09-2.79 (m, 3H), 2.61-2.51 (m, 2H), 2.15 (d, J=14.7 Hz, 6H). $^{13}$C NMR (100 MHz, DMSO) δ: 169.09, 167.61, 158.94, 153.63, 144.12, 133.16, 133.08, 119.60, 119.31, 118.95, 111.11, 109.44, 104.19, 60.21, 45.19, 32.08, 16.22, 12.89. ESI-MS: m/z 447.5 (M+18)$^+$, 452.3 (M+23)$^+$. C$_{23}$H$_{19}$N$_5$O$_2$S (429.13).

4-((2-((4-cyanophenyl)amino)-5,5-dioxido-7,8-dihydro-6H-thiopyrano[3,2-d]pyrimidin-4-yl)oxy)-3,5-dimethylbenzonitrile (IA-1-4)

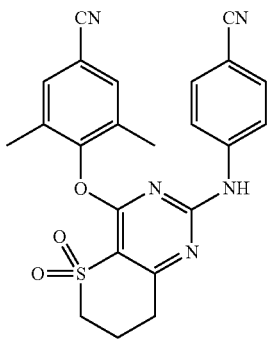

Compound IA-1-1 (100 mg, 0.24 mmol) was dissolved in CH$_2$Cl$_2$ (10 mL) and a mixture of mCPBA (125 mg, 0.73 mmol) was added at room temperature and stirred for 2 h. CH$_2$Cl$_2$ (50 mL) was added and washed with NaHSO$_3$ (30 mL) and H$_2$O (20 mL×2). Organic layer was washed with brine, dried with Na$_2$SO$_4$ and concentrated under reduced pressure. Recrystallized from MeOH/CHCl$_3$ to give compound IA-1-4 (67 mg, 62.2%) as a colorless crystal. mp 263-265° C. $^1$H NMR (400 MHz, DMSO-d$_6$) δ: 10.62 (s, 1H), 7.81 (s, 2H), 7.64-7.18 (m, 4H), 3.69-3.55 (m, 2H), 3.02 (t, J=6.0 Hz, 2H), 2.34 (d, J=5.1 Hz, 2H), 2.16 (s, 6H). $^{13}$C NMR (100 MHz, DMSO) δ: 169.89, 164.70, 158.49, 153.31, 143.82, 133.19, 133.08, 132.92, 119.52, 119.44, 118.92, 112.61, 109.52, 104.48, 52.49, 32.08, 18.98, 16.08. ESI-MS: m/z 463.5 (M+18)$^+$, 468.4 (M+23)$^+$. C$_{23}$H$_{19}$N$_5$O$_3$S (445.12).

Example 4. Preparation of Intermediate 9

3,5-dimethyl-4-((2-(piperidin-4-ylamino)-7,8-dihydro-6H-thiopyrano[3,2-d]pyrimidin-4-yl)oxy)benzonitrile (9a)

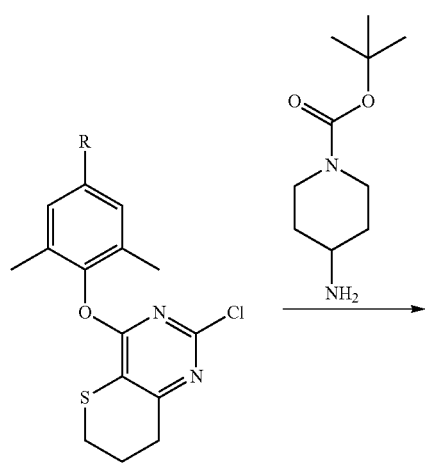

8a, R = CN
8b, R = CH$_3$
8c, R = CHCHCN

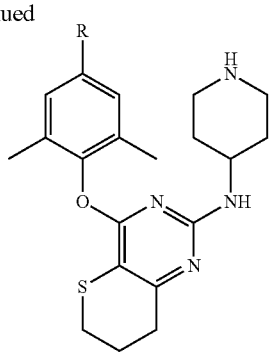

9a, R = CN
9b, R = CH$_3$
9c, R = CHCHCN

To a solution of 8a (2.00 g, 6.03 mmol) and N-Boc-4-piperidineamine (1.5 equiv) in NMP (10 mL), DIPEA (1.2 mL) was added and stirred at 100-120° C. for 4-6 h. After cooling, ethyl acetate was added to the reaction mixture. The ethyl acetate layer was washed with H$_2$O, dried over Na$_2$SO$_4$ and concentrated under reduced pressure. The residue was added TFA/CH$_2$Cl$_2$ (1:1) and stirred at room temperature for 4 hours. Saturated aqueous sodium bicarbonate was added to the reaction mixture to neutralize the residues. Ethyl acetate was added and organic layer was separated, washed with H$_2$O, dried over sodium sulfate and concentrated under reduced pressure. The crude material was purified by column chromatography over silica gel (200-300) with CH$_2$Cl$_2$/MeOH as an eluent to yield 3,5-dimethyl-4-((2-(piperidin-4-ylamino)-7,8-dihydro-6H-thiopyrano[3,2-d]pyrimidin-4-yl)oxy)benzonitrile (9a) as a white powder (1.5 g, 62.9%). mp>250° C. $^1$H NMR (400 MHz, DMSO-d$_6$) δ: 9.00 (s, 2H), 7.67 (s, 2H), 7.02 (s, 1H), 3.14 (d, J=12.5 Hz, 2H), 3.07-2.99 (m, 2H), 2.71 (t, J=6.3 Hz, 4H), 2.18-2.09 (m, 2H), 2.07 (s, 6H), 1.81 (s, 2H), 1.54 (s, 2H). $^{13}$C NMR (100 MHz, DMSO-d$_6$) δ: 163.27, 157.76, 154.08, 132.96, 132.77, 119.08, 108.60, 46.02, 41.99, 31.86, 28.05, 26.31, 23.39, 16.18. ESI-MS: m/z 396.4 (M+1)$^+$. C$_{21}$H$_{25}$N$_5$OS (395.18).

4-(mesityloxy)-N-(piperidin-4-yl)-7,8-dihydro-6H-thiopyrano[3,2-d]pyrimidin-2-amine (9b)

Synthesized in a similar procedure with intermediate 9a using 8b as starting material. Yield 28.7%, mp>290° C. $^1$H NMR (400 MHz, DMSO-d$_6$) δ: 8.91 (s, 2H), 6.90 (s, 3H), 3.15 (d, J=12.6 Hz, 2H), 3.07-2.96 (m, 2H), 2.69 (t, J=6.3 Hz, 4H), 2.24 (s, 3H), 2.12 (p, J=5.9 Hz, 2H), 1.98 (s, 6H), 1.82 (s, 2H), 1.54 (s, 2H). $^{13}$C NMR (100 MHz, DMSO-d$_6$) δ: 164.00, 157.90, 147.95, 134.59, 130.15, 129.29, 46.06, 42.15, 31.84, 28.14, 26.30, 23.45, 20.81, 16.44. ESI-MS: m/z 385.5 (M+1)$^+$. C$_{21}$H$_{28}$N$_4$OS (384.20).

(E)-3-(3,5-dimethyl-4-((2-(piperidin-4-ylamino)-7,8-dihydro-6H-thiopyrano[3,2-d]pyrimidin-4-yl)oxy)phenyl)acrylonitrile (9c)

Synthesized in a similar procedure with intermediate 9a using 8c as starting material. Yield 54.2%, mp>280° C. $^1$H NMR (400 MHz, DMSO-d$_6$) δ: 8.85 (s, 2H), 7.59 (d, J=16.7 Hz, 1H), 7.43 (s, 2H), 7.30 (s, 2H), 6.66 (s, 1H), 6.40 (d, J=16.7 Hz, 1H), 3.43 (s, 2H), 3.08-2.95 (m, 2H), 2.68 (t, J=6.2 Hz, 4H), 2.15-2.09 (m, 2H), 2.06 (s, 1H), 2.03 (s, 6H), 1.61 (s, 4H), 1.32 (s, 2H). $^{13}$C NMR (100 MHz, DMSO-d$_6$) δ: 163.65, 158.05, 152.59, 150.58, 131.62, 131.45, 126.05, 119.42, 96.51, 62.02, 52.67, 49.07, 31.89, 26.34, 23.50, 16.46. ESI-MS: m/z 422.5 (M+1)$^+$. C$_{23}$H$_{27}$N$_5$OS (421.19).

Example 5. Preparation of Compounds IIA-1

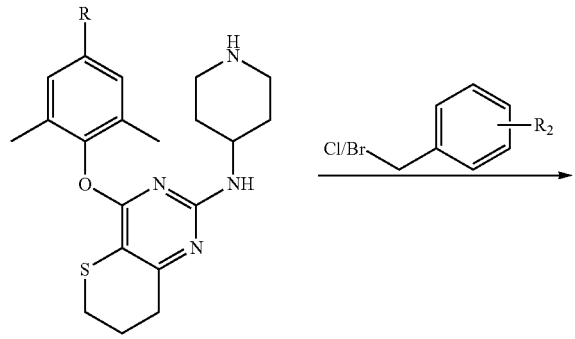

9a, R = CN
9b, R = CH$_3$
9c, R = CHCHCN

To a solution of 9a (0.20 g, 0.51 mmol) in DMF (10 mL), K$_2$CO$_3$ (0.19 g, 0.76 mmol) and 4-(bromomethyl)benzenesulfonamide (0.11 g, 0.76 mmol) were added and stirred overnight. The reaction mixture was concentrated under reduced pressure. Ethyl acetate was added to the reaction mixture. The ethyl acetate layer was washed with H$_2$O, dried over Na$_2$SO$_4$ and concentrated under reduced pressure. The crude material was purified by column chromatography over silica gel (200-300 mesh) with CH$_2$Cl$_2$/MeOH as an eluent and washed with MeOH to afford the corresponding compounds as white powder (0.24 g, 84.1%). mp 193-195° C. $^1$H NMR (400 MHz, DMSO-d$_6$) δ 7.77 (d, J=8.3 Hz, 2H), 7.66 (s, 2H), 7.45 (d, J=8.0 Hz, 2H), 7.30 (s, 2H), 6.88 (s, 1H), 3.45 (s, 2H), 3.13-2.95 (m, 2H), 2.91-2.57 (m, 4H), 2.16-2.08 (m, 2H), 2.06 (s, 6H), 1.99-0.81 (m, 6H). $^{13}$C NMR (100 MHz, DMSO) δ 163.25, 157.97, 154.22, 143.35, 143.13, 133.02, 132.66, 129.41, 126.04, 119.10, 108.56, 61.97, 52.61, 49.07, 31.86, 31.65, 26.34, 23.48, 16.15. ESI-MS: m/z 565.5 (M+1)$^+$. C$_{28}$H$_{32}$N$_6$O$_3$S$_2$ (564.20).

Synthesized of IIA-1-2-IIA-1-13 in a similar procedure to IIA-1-1 using the appropriate starting material.

4-((4-((4-(mesityloxy)-7,8-dihydro-6H-thiopyrano[3,2-d]pyrimidin-2-yl)amino) piperidin-1-yl)methyl) benzenesulfonamide (IIA-1-2)

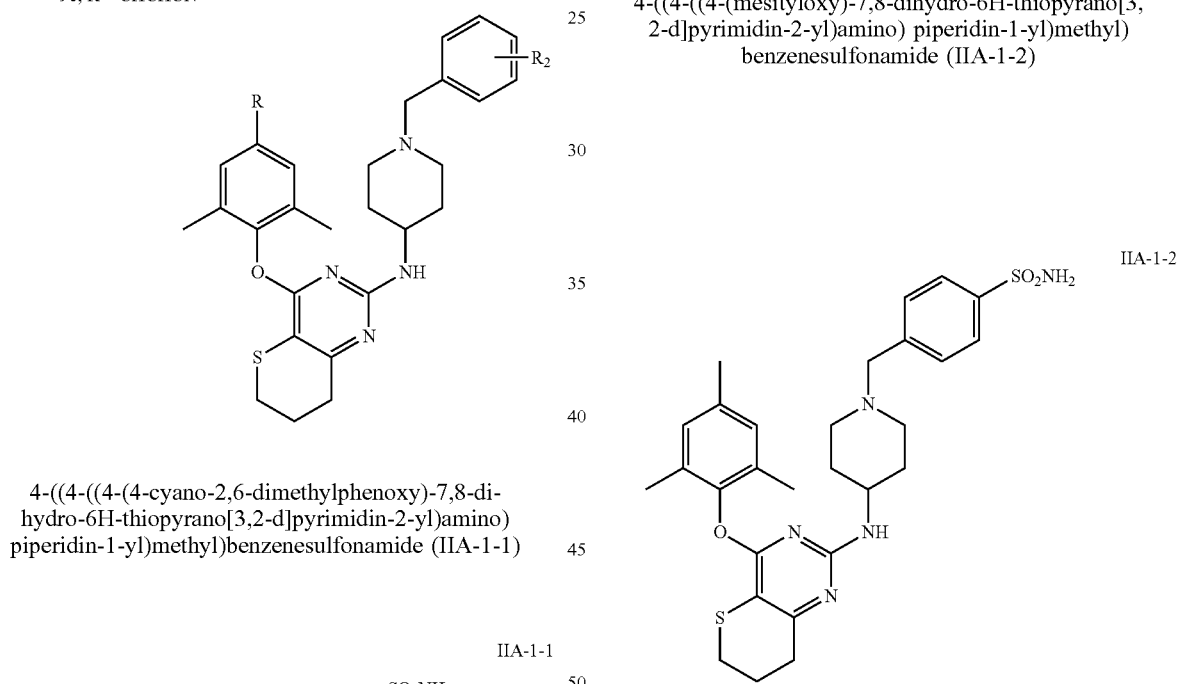

4-((4-((4-(4-cyano-2,6-dimethylphenoxy)-7,8-dihydro-6H-thiopyrano[3,2-d]pyrimidin-2-yl)amino) piperidin-1-yl)methyl)benzenesulfonamide (IIA-1-1)

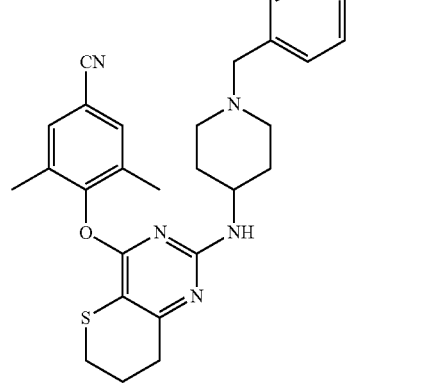

Starting with 9b (0.25 g, 0.65 mmol) and 4-(bromomethyl)benzenesulfonamide (0.20 mg, 0.78 mmol) to afford IIA-1-2 (157 mg, 43.6%) as a white powder. mp 218-220° C. $^1$H NMR (400 MHz, DMSO-d$_6$) δ 7.77 (d, J=8.3 Hz, 2H), 7.44 (d, J=8.0 Hz, 2H), 7.30 (s, 2H), 6.88 (s, 2H), 6.60 (s, 1H), 3.45 (s, 2H), 3.08-2.91 (m, 2H), 2.79-2.57 (m, 4H), 2.23 (s, 3H), 2.10 (dt, J=11.8, 5.4 Hz, 2H), 1.97 (s, 6H), 1.72-1.47 (m, 2H), 1.46-1.10 (m, 2H). $^{13}$C NMR (100 MHz, DMSO) δ 163.97, 162.36, 158.15, 148.02, 143.36, 143.13, 134.49, 130.15, 129.42, 129.22, 126.03, 61.99, 52.65, 49.07, 31.86, 31.74, 26.33, 23.54, 20.80, 16.43. ESI-MS: m/z 554.5 (M+1)$^+$. C$_{28}$H$_{35}$N$_5$O$_3$S$_2$ (553.22).

(E)-4-((4-((4-(2-cyanovinyl)-2,6-dimethylphenoxy)-7,8-dihydro-6H-thiopyrano[3,2-d]pyrimidin-2-yl)amino)piperidin-1-yl)methyl)benzenesulfonamide (IIA-1-3)

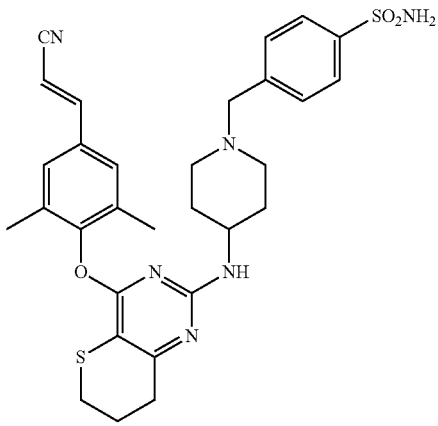

Starting with 9c (0.20 g, 0.47 mmol) and 4-(bromomethyl)benzenesulfonamide (0.14 g, 0.57 mmol) to afford IIA-1-3 (0.18 g, 64.2%) as a white powder. mp 237-239° C. $^1$H NMR (400 MHz, DMSO-d$_6$) δ 7.77 (d, J=8.3 Hz, 2H), 7.59 (d, J=16.7 Hz, 1H), 7.43 (s, 4H), 7.30 (s, 2H), 6.66 (s, 1H), 6.40 (d, J=16.7 Hz, 1H), 3.43 (s, 2H), 3.08-2.95 (m, 2H), 2.68 (t, J=6.2 Hz, 4H), 2.15-2.09 (m, 2H), 2.06 (s, 1H), 2.03 (s, 6H), 1.61 (s, 4H), 1.32 (s, 2H). $^{13}$C NMR (100 MHz, DMSO) δ 163.65, 158.05, 152.59, 150.58, 143.41, 143.14, 131.62, 131.45, 129.43, 128.33, 126.05, 119.42, 96.51, 62.02, 52.67, 49.07, 31.89, 31.68, 26.34, 23.50, 16.46. ESI-MS: m/z 591.2257 (M+1)$^+$. C$_{30}$H$_{34}$N$_6$O$_3$S$_2$ (590.2134).

3-((4-((4-(4-cyano-2,6-dimethylphenoxy)-7,8-dihydro-6H-thiopyrano[3,2-d] pyrimidin-2-yl)amino)piperidin-1-yl)methyl)benzenesulfonamide (IIA-1-4)

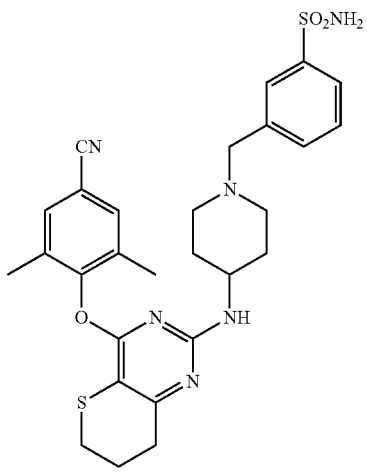

Starting with 9a (0.20 g, 0.51 mmol) and 3-(bromomethyl)benzenesulfonamide (0.15 g, 0.61 mmol) to afford IIA-1-4 (0.21 g, 73.5%) as a white solid. mp 170-172° C. $^1$H NMR (400 MHz, DMSO-d$_6$) δ 7.74 (s, 1H), 7.71 (d, J=7.4 Hz, 1H), 7.67 (s, 2H), 7.51 (t, J=7.5 Hz, 1H), 7.47 (d, J=7.5 Hz, 1H), 7.36 (s, 2H), 6.80 (s, 1H), 3.46 (s, 2H), 3.02 (dd, J=6.7, 4.1 Hz, 2H), 2.69 (t, J=6.1 Hz, 4H), 2.19-2.09 (m, 2H), 2.08 (s, 1H), 2.06 (s, 6H), 1.66 (s, 4H), 1.32 (s, 2H). $^{13}$C NMR (100 MHz, DMSO) δ 163.25, 157.84, 154.22, 144.59, 144.09, 140.31, 133.01, 132.74, 132.47, 129.26, 125.92, 124.68, 119.13, 108.55, 62.05, 52.62, 49.07, 31.82, 31.65, 26.30, 23.45, 16.18. ESI-MS: m/z 565.2045 (M+1)$^+$. C$_{28}$H$_{32}$N$_6$O$_3$S$_2$ (564.1977).

4-((2-((1-(4-cyanobenzyl)piperidin-4-yl)amino)-7,8-dihydro-6H-thiopyrano[3,2-d] pyrimidin-4-yl)oxy)-3,5-dimethylbenzonitrile (IIA-1-5)

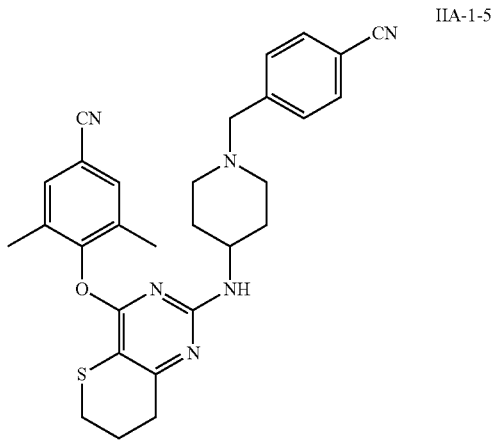 [SMILES: Cc1cc(C#N)cc(C)c1Oc1nc(NC2CCN(Cc3ccc(C#N)cc3)CC2)nc2c1SCCC2]

Starting with 9a (0.20 g, 0.51 mmol) and 4-(chloromethyl)benzonitrile (92 mg, 0.61 mmol) to afford IIA-1-5 (0.21 g, 81.3%) as a white solid. mp 184-186° C. $^1$H NMR (400 MHz, DMSO-d$_6$) δ 7.77 (d, J=8.2 Hz, 2H), 7.66 (s, 2H), 7.47 (d, J=8.1 Hz, 2H), 6.89 (br, 1H), 3.48 (s, 2H), 3.12-2.95 (m, 2H), 2.69 (t, J=6.3 Hz, 5H), 2.19-2.02 (m, 8H), 1.63 (s, 4H), 1.32 (s, 2H). $^{13}$C NMR (100 MHz, DMSO) δ 163.26, 158.00, 154.22, 145.26, 133.01, 132.66, 132.58, 129.87, 119.38, 119.10, 110.08, 108.56, 61.93, 52.59, 48.66, 31.84, 31.66, 26.33, 23.47, 16.16. ESI-MS: m/z 511.6 (M+1)$^+$. C$_{29}$H$_{30}$N$_6$OS (510.22).

4-((2-((1-(3-cyanobenzyl)piperidin-4-yl)amino)-7,8-dihydro-6H-thiopyrano[3,2-d] pyrimidin-4-yl)oxy)-3,5-dimethylbenzonitrile (IIA-1-6)

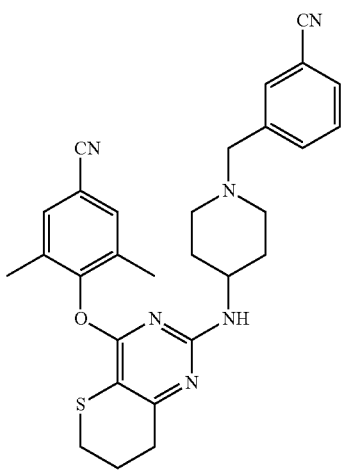

IIA-1-6

Starting with 9a (0.20 g, 0.51 mmol) and 4-(bromomethyl)benzonitrile (119 mg, 0.61 mmol) to afford IIA-1-6 (0.21 g, 81.3%) as a white solid. mp 164-166° C. $^1$H NMR (400 MHz, DMSO-d$_6$) δ 7.72 (d, J=7.6 Hz, 1H), 7.68 (s, 1H), 7.65 (s, 2H), 7.62 (d, J=7.8 Hz, 1H), 7.53 (t, J=7.7 Hz, 1H), 6.87 (s, 1H), 3.45 (s, 2H), 3.09-2.94 (m, 2H), 2.69 (t, J=6.3 Hz, 4H), 2.19-2.09 (m, 2H), 2.09 (s, 1H), 2.06 (s, 6H), 1.63 (s, 4H), 1.31 (s, 2H). $^{13}$C NMR (100 MHz, DMSO) δ 163.26, 157.96, 154.22, 140.90, 134.02, 133.02, 132.68, 132.44, 131.22, 129.89, 119.34, 119.10, 111.65, 108.56, 61.46, 55.38, 52.49, 31.86, 31.64, 31.15, 26.33, 23.47, 21.52, 16.16. ESI-MS: m/z 511.2335 (M+1)$^+$. C$_{29}$H$_{30}$N$_6$OS (510.2202).

4-((2-((1-(2-cyanobenzyl)piperidin-4-yl)amino)-7,8-dihydro-6H-thiopyrano[3,2-d] pyrimidin-4-yl)oxy)-3,5-dimethylbenzonitrile (IIA-1-7)

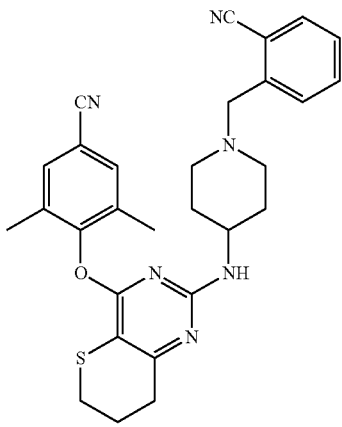

IIA-1-7

Starting with 9a (0.20 g, 0.51 mmol) and 4-(chloromethyl)benzonitrile (92 mg, 0.61 mmol) to afford IIA-1-7 (0.20 g, 77.5%) as a white crystal. mp 206-208° C. $^1$H NMR (400 MHz, DMSO-d$_6$) δ 7.79 (d, J=7.6 Hz, 1H), 7.70-7.61 (m, 3H), 7.52 (d, J=7.7 Hz, 1H), 7.46 (t, J=7.6 Hz, 1H), 6.86 (s, 1H), 3.56 (s, 2H), 3.10-2.94 (m, 2H), 2.69 (t, J=6.2 Hz, 4H), 2.17-2.09 (m, 2H), 2.09 (s, 1H), 2.06 (s, 6H), 1.59 (s, 4H), 1.30 (s, 2H). $^{13}$C NMR (100 MHz, DMSO) δ 163.26, 158.00, 154.22, 142.82, 133.42, 133.41, 133.02, 132.69, 130.48, 128.36, 119.08, 118.11, 112.53, 108.57, 60.36, 60.22, 52.54, 31.88, 31.58, 31.19, 26.33, 23.47, 16.17, 14.56. ESI-MS: m/z 511.3 (M+1)$^+$. C$_{29}$H$_{30}$N$_6$OS (510.22).

4-((4-((4-(4-cyano-2,6-dimethylphenoxy)-7,8-dihydro-6H-thiopyrano[3,2-d]pyrimidin-2-yl)amino)piperidin-1-yl)methyl)benzamide (IIA-1-8)

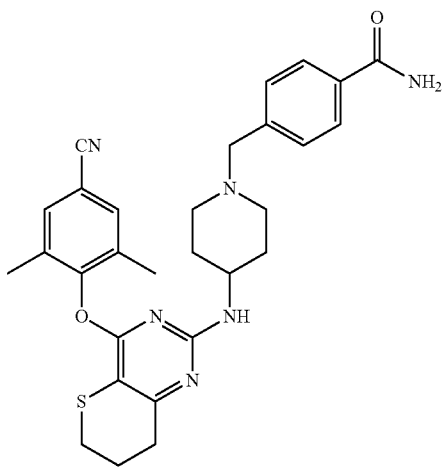

IIA-1-8

Starting with 9a (0.20 g, 0.51 mmol) and 4-(chloromethyl)benzamide (103 mg, 0.61 mmol) to afford IIA-1-8 (0.20 g, 74.8%) as a white crystal. mp 261-263° C. $^1$H NMR (400 MHz, DMSO-d$_6$) δ 7.91 (s, 1H), 7.81 (d, J=8.1 Hz, 2H), 7.66 (s, 2H), 7.33 (d, J=7.9 Hz, 2H), 7.30 (s, 1H), 6.86 (br, 1H), 3.43 (s, 2H), 3.08-2.94 (m, 2H), 2.69 (t, J=6.2 Hz, 4H), 2.17-2.10 (m, 2H), 2.09 (s, 1H), 2.06 (s, 6H), 1.60 (s, 4H), 1.31 (s, 2H). $^{13}$C NMR (100 MHz, DMSO) δ 168.25, 163.26, 158.04, 154.23, 142.60, 142.52, 133.45, 133.02, 132.69, 128.88, 127.88, 119.11, 108.56, 79.65, 62.19, 52.63, 31.84, 31.65, 31.16, 26.33, 23.47, 16.16. ESI-MS: m/z 529.5 (M+1)$^+$, 551.6 (M+23)$^+$. C$_{29}$H$_{32}$N$_6$O$_2$S (528.23).

3-((4-((4-(4-cyano-2,6-dimethylphenoxy)-7,8-dihydro-6H-thiopyrano[3,2-d] pyrimidin-2-yl)amino)piperidin-1-yl)methyl)benzamide (IIA-1-9)

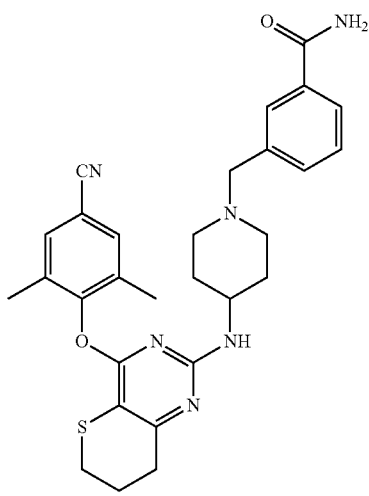

Starting with 9a (0.20 g, 0.51 mmol) and 3-(chloromethyl)benzamide (103 mg, 0.61 mmol) to afford IIA-1-9 (0.19 g, 71.1%) as a white solid. mp 245-247° C. $^1$H NMR (400 MHz, DMSO-d$_6$) δ 7.95 (s, 1H), 7.76 (d, J=11.6 Hz, 2H), 7.66 (s, 2H), 7.39 (d, J=7.3 Hz, 2H), 7.33 (s, 1H), 6.86 (s, 1H), 3.43 (s, 2H), 3.02 (s, 2H), 2.77-2.58 (m, 4H), 2.19-2.09 (m, 2H), 2.09 (s, 1H), 2.06 (s, 6H), 1.63 (s, 4H), 1.32 (s, 2H). $^{13}$C NMR (100 MHz, DMSO) δ 168.43, 163.26, 157.96, 154.22, 139.22, 134.68, 133.02, 132.68, 132.03, 128.45, 126.44, 119.10, 108.56, 62.44, 52.60, 48.81, 31.87, 31.65, 31.15, 26.33, 23.47, 16.16. ESI-MS: m/z 529.4 (M+1)$^+$, 551.6 (M+23)$^+$. C$_{29}$H$_{32}$N$_6$O$_2$S (528.23).

ethyl 4-((4-((4-(4-cyano-2,6-dimethylphenoxy)-7,8-dihydro-6H-thiopyrano[3,2-d] pyrimidin-2-yl)amino)piperidin-1-yl)methyl)benzoate (IIA-1-10)

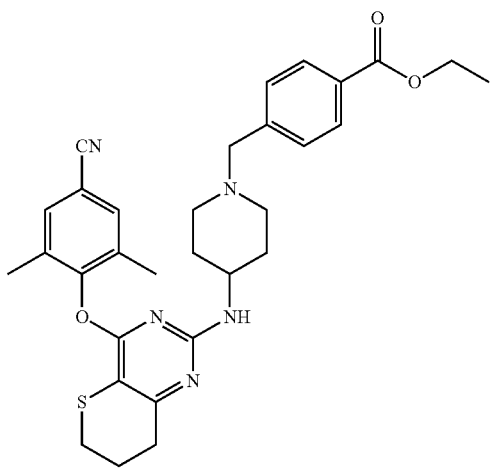

Starting with 9a (0.2 g, 0.51 mmol) and ethyl 4-(chloromethyl)benzoate (0.15 g, 0.61 mmol) to afford IIA-1-10 (0.16 g, 56.7%) as a white solid. mp 181-183° C. $^1$H NMR (400 MHz, DMSO-d$_6$) δ 7.91 (d, J=8.1 Hz, 2H), 7.65 (s, 2H), 7.41 (d, J=8.1 Hz, 2H), 6.87 (br, 1H), 4.30 (q, J=7.1 Hz, 2H), 3.46 (s, 2H), 3.09-2.97 (m, 2H), 2.69 (t, J=6.2 Hz, 4H), 2.16-2.09 (m, 2H), 2.09 (s, 1H), 2.06 (s, 6H), 1.60 (s, 4H), 1.31 (t, J=7.1 Hz, 5H). $^{13}$C NMR (100 MHz, DMSO) δ 166.11, 163.26, 157.99, 154.24, 144.87, 141.04, 133.02, 132.74, 129.52, 129.29, 128.98, 119.10, 108.56, 62.16, 61.04, 56.50, 52.62, 31.88, 31.65, 31.16, 26.33, 23.47, 16.15, 14.66. ESI-MS: m/z 558.6 (M+1)$^+$. C$_{31}$H$_{35}$N$_5$O$_3$S (557.25).

3,5-dimethyl-4-((2-((1-(4-(methylsulfonyl)benzyl)piperidin-4-yl)amino)-7,8-dihydro-6H-thiopyrano[3,2-d]pyrimidin-4-yl)oxy)benzonitrile (IIA-1-11)

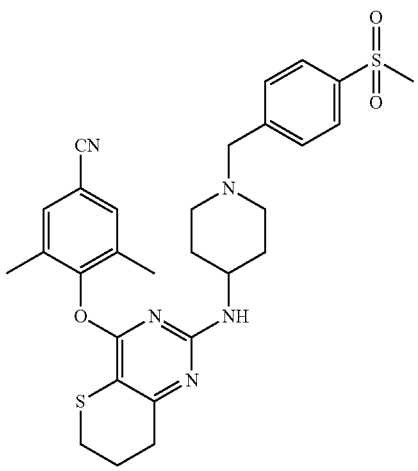

Starting with 9a (0.20 g, 0.51 mmol) and 1-(chloromethyl)-4-(methylsulfonyl)benzene (0.15 g, 0.61 mmol) to afford IIA-1-11 (0.19 g, 66.7%) as a white solid. mp 265-267° C. $^1$H NMR (400 MHz, DMSO-d$_6$) δ 7.87 (d, J=8.3 Hz, 2H), 7.66 (s, 2H), 7.54 (d, J=8.2 Hz, 2H), 6.89 (br, 1H), 3.50 (s, 2H), 3.20 (s, 3H), 3.10-2.95 (m, 2H), 2.69 (t, J=6.2 Hz, 4H), 2.11 (m, 2H), 2.09 (s, 1H), 2.06 (s, 6H), 1.64 (s, 4H), 1.32 (s, 2H). $^{13}$C NMR (100 MHz, DMSO) δ 163.26, 158.00, 157.98, 154.22, 145.46, 139.81, 133.02, 132.69, 129.77, 127.39, 119.12, 108.56, 61.89, 52.65, 48.68, 44.07, 31.86, 31.66, 26.33, 23.47, 16.16. ESI-MS: m/z 564.5 (M+1)$^+$, 586.5 (M+23)$^+$. C$_{29}$H$_{33}$N$_5$O$_3$S$_2$ (563.20).

3,5-dimethyl-4-((2-((1-(4-nitrobenzyl)piperidin-4-yl)amino)-7,8-dihydro-6H-thiopyrano[3,2-d]pyrimidin-4-yl)oxy)benzonitrile (IIA-1-12)

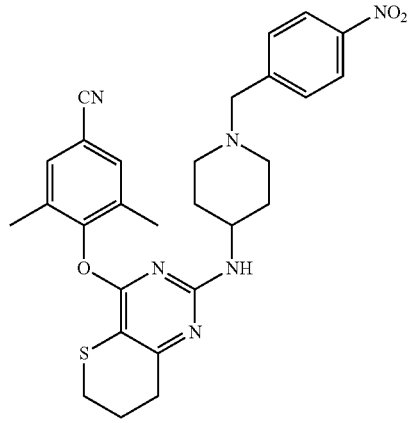

Starting with 9a (0.20 g, 0.51 mmol) and 1-(chloromethyl)-4-nitrobenzene (0.13 g, 0.61 mmol) to afford IIA-1-12 (0.14 g, 52.2%) as a white solid. mp 190-192° C. $^1$H NMR (400 MHz, DMSO-$d_6$) δ 8.18 (d, J=8.7 Hz, 2H), 7.66 (s, 2H), 7.55 (d, J=8.6 Hz, 2H), 6.88 (s, 1H), 3.53 (s, 2H), 3.11-2.92 (m, 2H), 2.69 (t, J=6.2 Hz, 4H), 2.19-2.10 (m, 2H), 2.09 (s, 1H), 2.06 (s, 6H), 1.59 (s, 4H), 1.33 (s, 2H). $^{13}$C NMR (100 MHz, DMSO) δ 163.26, 157.99, 154.23, 147.51, 146.97, 133.02, 132.67, 130.03, 123.80, 119.10, 108.56, 61.63, 52.61, 31.84, 31.66, 31.15, 26.33, 23.47, 19.03, 16.15. ESI-MS: m/z 531.5 (M+1)$^+$. $C_{28}H_{30}N_6O_3S$ (530.21).

Example 6. Preparation of 4-((2-((1-(4-aminobenzyl)piperidin-4-yl)amino)-7,8-dihydro-6H-thiopyrano[3,2-d]pyrimidin-4-yl)oxy)-3,5-dimethylbenzonitrile (IIA-1-13)

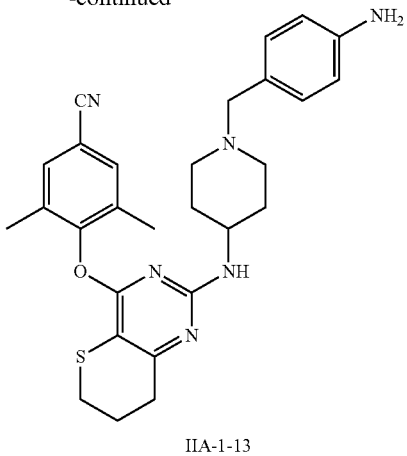

To a solution of Fe powder (0.56 g, 10 mmol) and NH$_4$Cl (55 mg, 1 mmol) in H$_2$O (5 mL) was added AcOH (0.12 mL), the mixture was heated to 50° C. for 15 min. A solution of IIA-1-12 (0.53 g, 1.0 mmol) in DMF (5 mL) was added and stirred for another 15 min. After cooling to the room temperature, pH was adjusted to >9 with NaHCO$_3$, and residue was filtered over diatomite. H$_2$O (50 mL) was added to the filtrate and extracted with ethyl acetate (20 mL×3) and the combined organic layer was washed with brine, dried over Na$_2$SO$_4$ and evaporated to dryness. The residue was purified by silica gel column chromatography using MeOH/CH$_2$Cl$_2$ as an eluent to afford IIA-1-13 (0.31 g, 63.6%) as a white solid. mp 169-171° C. $^1$H NMR (400 MHz, DMSO-$d_6$) δ 7.66 (s, 2H), 6.87 (d, J=8.1 Hz, 2H), 6.49 (d, J=8.2 Hz, 2H), 4.94 (s, 2H), 3.17 (s, 2H), 3.08-2.95 (m, 2H), 2.68 (t, J=6.1 Hz, 4H), 2.12 (d, J=5.3 Hz, 2H), 2.09 (s, 1H), 2.05 (s, 6H), 1.48 (s, 4H), 1.23 (s, 2H). $^{13}$C NMR (100 MHz, DMSO) δ 163.24, 158.03, 154.22, 147.95, 133.01, 132.65, 130.16, 125.66, 123.82, 119.11, 114.01, 108.55, 62.55, 52.39, 31.65, 26.31, 23.46, 21.24, 19.03, 16.16, 14.56. ESI-MS: m/z 501.5 (M+1)$^+$. $C_{28}H_{32}N_6OS$ (500.24).

Example 7. Preparation of N-(4-((4-((4-(4-cyano-2,6-dimethylphenoxy)-7,8-dihydro-6H-thiopyrano[3,2-d]pyrimidin-2-yl)amino)piperidin-1-yl)methyl)phenyl) methanesulfonamide (IIA-1-14)

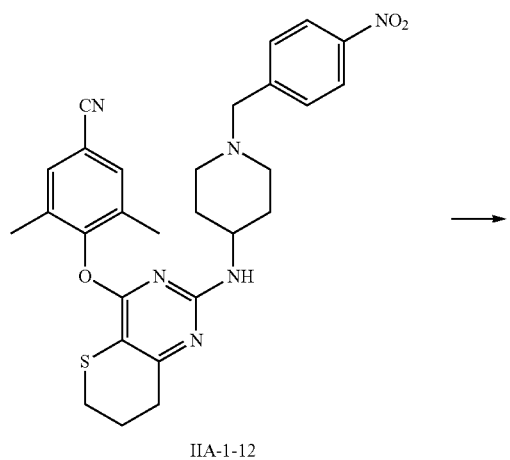 → 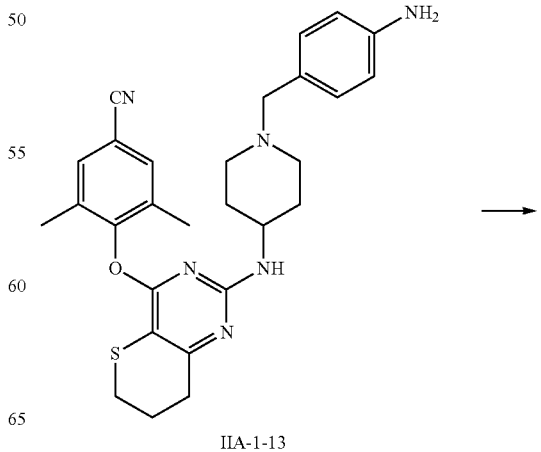 →

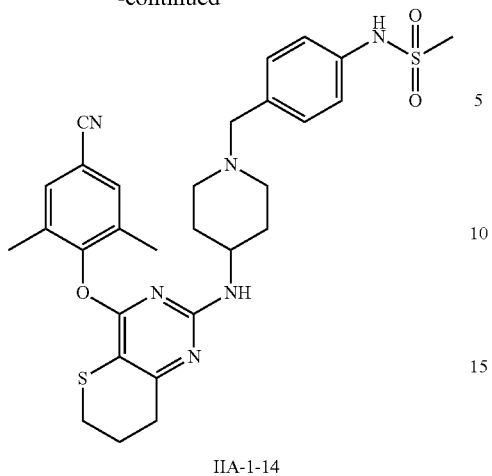

IIA-1-14

To a solution of IIA-1-13 (100 mg, 0.2 mmol) and Et₃N (61 mg, 0.6 mmol) in CH₂Cl₂ in an ice bath was added a solution of methanesulfonyl chloride (69 mg, 0.6 mmol) and stirred for 4 h. H₂O (15 mL) was added to the solution and pH was adjusted to >7 with NaHCO₃, then extracted with ethyl acetate (15 mL×3) and the combined organic layer was washed with brine, dried over Na₂SO₄ and evaporated to dryness. The crude product was recrystallized from MeOH/CHCl₃ to afford IIA-1-14 (20 mg, 17.3%) as white solid. mp 153-157° C. $^1$H NMR (400 MHz, DMSO-d₆) δ 9.68 (s, 1H), 7.66 (s, 2H), 7.21 (d, J=8.3 Hz, 2H), 7.14 (d, J=8.4 Hz, 2H), 6.70 (br, 1H), 3.32 (s, 2H), 3.07-2.99 (m, 2H), 2.96 (s, 3H), 2.69 (t, J=6.3 Hz, 4H), 2.11 (t, J=5.7 Hz, 2H), 2.09 (s, 1H), 2.06 (s, 6H), 1.55 (s, 4H), 1.23 (s, 2H). $^{13}$C NMR (100 MHz, DMSO) δ 163.25, 137.49, 134.60, 133.01, 132.90, 132.77, 132.70, 130.12, 120.24, 119.13, 108.54, 100.98, 62.08, 52.56, 39.62, 36.25, 31.81, 31.63, 31.17, 26.30, 23.45, 16.16. ESI-MS: m/z 579.2250 (M+1)⁺. C₂₉H₃₄N₆O₃S₂ (578.2134).

Example 8. Preparation of IIC-1

4-((2-((1-(3-cyanophenyl)piperidin-4-yl)amino)-7,8-dihydro-6H-thiopyrano[3,2-d] pyrimidin-4-yl)oxy)-3,5-dimethylbenzonitrile (IIC-1-1)

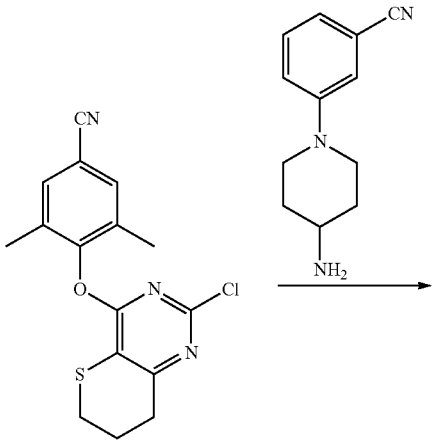

To a solution of 8a (0.20 g, 0.6 mmol) and 3-(4-aminopiperidin-1-yl)benzonitrile (145 mg, 0.72 mmol) in NMP (5 mL), DIPEA (120 μL) was added, the mixture was then heated to 100° C. overnight. The mixture was cooled to room temperature; H₂O was added and stirred for 30 min. The product was filtered to recrystallized from MeOH/CHCl₃ to give the white solid (129 mg, 43.1%). mp 186-187° C. $^1$H NMR (400 MHz, DMSO-d₆) δ 7.65 (s, 2H), 7.34 (dd, J=8.5, 7.4, 1H), 7.26 (s, 1H), 7.21 (d, J=8.5 Hz, 1H), 7.09 (d, J=7.4 Hz, 1H), 6.82 (br, 1H), 3.67 (s, 3H), 3.11-2.94 (m, 2H), 2.70 (t, J=6.0 Hz, 3H), 2.12 (t, J=5.7 Hz, 2H), 2.08 (s, 1H), 2.07 (s, 6H), 1.69 (s, 2H), 1.35 (s, 2H). $^{13}$C NMR (100 MHz, DMSO) δ 163.26, 157.91, 154.17, 151.25, 133.01, 132.73, 130.64, 121.53, 120.26, 119.84, 119.12, 118.11, 112.37, 108.58, 56.52, 47.19, 31.85, 31.16, 30.82, 26.31, 23.42, 18.98, 16.18. ESI-MS: m/z 497.2133 (M+1)⁺. C₂₈H₂₈N₆OS (496.2045).

3-(4-((4-(4-cyano-2,6-dimethylphenoxy)-7,8-dihydro-6H-thiopyrano[3,2-d] pyrimidin-2-yl)amino) piperidin-1-yl)benzamide (IIC-1-2)

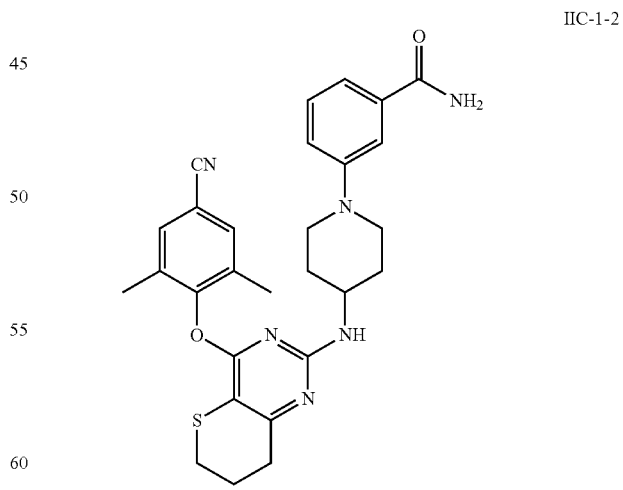

IIC-1-2

Synthesized of IIC-1-2 in a similar procedure with IIC-1-1 using the 3-(4-aminopiperidin-1-yl)benzamide as starting material. Yield 35.1%, mp 232-234° C. $^1$H NMR (400 MHz, DMSO-d₆) δ 7.91 (s, 1H), 7.68 (s, 2H), 7.38 (s, 1H), 7.29 (s, 1H), 7.25 (s, 1H), 7.23 (s, 1H), 7.03 (d, J=4.1 Hz, 2H), 6.73 (s, 1H), 3.65 (s, 2H), 3.03 (d, J=5.4 Hz, 2H), 2.72 (t, J=6.3 Hz, 3H), 2.13 (t, J=5.7 Hz, 2H), 2.09 (s, 1H), 2.09 (s, 6H), 1.72 (s, 2H), 1.42 (s, 2H). $^{13}$C NMR (100 MHz, DMSO) δ 168.71, 163.27, 157.95, 154.18, 151.18, 135.40, 133.01, 132.75, 129.25, 119.11, 118.66, 117.98, 115.09, 108.58, 56.50, 48.06, 31.88, 31.16, 26.32, 23.46, 19.04, 16.21. ESI-MS: m/z 515.2226 (M+1)$^+$. $C_{28}H_{30}N_6O_2S$ (514.2151).

Example 9. In Vitro Anti-HIV Activity of Compounds

Selected compounds were screened for inhibitory activity against HIV-1 using MTT method as describe previously by Christophe. Pannecouque et al. *Nat. Protoc.* 3 (2008) 427-434, and Rudi Pauwels et al. *J. Virol. Methods* 20 (1988) 309-321. Briefly, MT-4 cells infected with HIV-1 can only survive for 5 to 7 days without any treatment, but when HIV-1 inhibitors were added, they can protect MT-4 cell from cytopathic. Serial solution of compounds was added to MT-4 cells after infected with HIV-1, MTT method was used to detect the survival rate after culture for 5 to 7 days. $EC_{50}$ value was defined as compound concentration required to achieve 50% protection of MT-4 cells against HIV-1-induced cytopathic effect. In vitro anti-HIV-1 assay was supported by Rega Institute for Medical Research.

1. Materials:
   (1) MT-4 cells infected with HIV-1 viral strains (IIIB, L100I, K103N, Y181C, Y188L, E138K, F227L/V106A, Y181C/K103N) were provided by Rega Institute for Medical Research, Katholieke Universiteit Leuven, Belgium.
   (2) MTT and formazan: sigma Chemical Co.
   (3) Preparation of compounds: Stock solutions (10×final concentration) of test compounds is diluted with double distilled water for 5 folds and 5 concentrations of one compound are prepared.
   (4) Reference drugs: Nevirapine (NVP), Efavirenz (EFV), Etravirine (ETV), Rilpivirine (RPV) and Azidothymidine (AZT).
   (5) Method (MTT method): Serial five-fold dilutions of test compounds were added to cultured MT-4 cells infected with HIV-1, after 5 to 7 days, MTT was added and cultured for a few hours. Medium was removed and lysate was added followed by formazan, OD value was determined in 690 nm and 540 nm by microplate reader, and $EC_{50}$ value was calculated.

2. Method

The MTT method was described briefly as follows: 96-well plastic microtiter trays were filled with 100 μL of complete medium. Subsequently, serial of tested compounds was added (25 μL) to two series of triplicate wells so as to allow simultaneous evaluation of their effects on HIV- and mock infected cells. 50 μL of 1×10$^4$ cells/mL MT-4 cells were added. After cultured for 5 days at 37° C. in humidified atmosphere in the presence of 5% $CO_2$, MTT was added and cultured for another 2 h, then medium was removed and 100 μL isopropanol solution was added to lyse the cells. Formazan crystals were added and vibrated platform shaker for 10 min to solubilize the formazan crystals. Absorbances at 690 nm and 540 nm were read by using spectrophotometrically. $EC_{50}$ was defined as the concentration achieving 50% protection from the cytopathic effect of the virus in infected cells.

2. Biological Data for Selected Compounds

Selected compounds prepared as described above were assayed in MT-4 cells infected with wide-type III$_B$, L100I, K103N, Y181C, Y188L, E138K or double mutant RES056 (Y181C/K103N) and F227L/V106A HIV-1 strains. Nevirapine, Efavirenz, Etravirine, Rilpivirine and Azidothymidine were selected as reference drugs. The results were listed below as $EC_{50}$ value (nM)

| Compds | wt | L100I | K103N | Y181C | Y188L | E138K | F227L/V106A | Y181C/K103N |
|---|---|---|---|---|---|---|---|---|
| IA-1-1 | A | B | A | B | B | B | B | B |
| IA-1-2 | A | A | A | B | B | B | B | B |
| IA-1-3 | A | C | B | B | B | B | C | C |
| IA-1-4 | A | B | A | B | B | B | B | B |
| IIA-1-1 | A | B | A | B | A | A | B | B |
| IIA-1-2 | A | B | A | B | B | B | B | C |
| IIA-1-3 | A | A | A | A | B | B | A | B |
| IIA-1-4 | A | C | B | B | B | B | B | C |
| IIA-1-5 | A | B | B | B | B | B | C | C |
| IIA-1-6 | A | C | B | B | B | B | C | C |
| IIA-1-7 | A | C | B | B | C | B | C | C |
| IIA-1-8 | A | B | A | B | B | B | C | B |
| IIA-1-9 | A | B | B | B | B | B | C | C |
| IIA-1-10 | B | C | B | C | C | C | C | C |
| IIA-1-11 | A | B | A | B | B | B | B | B |
| IIA-1-12 | A | C | B | C | B | B | C | C |
| IIA-1-13 | A | B | A | B | B | B | C | C |
| IIA-1-14 | A | B | A | A | B | A | C | C |
| IIC-1-1 | B | C | B | C | C | C | C | C |
| IIC-1-2 | A | B | A | A | A | B | C | B |
| NVP | C | C | C | C | C | C | C | C |
| EFV | A | B | B | A | B | A | B | C |
| ETV | A | A | A | B | B | B | B | B |
| RPV | A | A | A | A | B | A | B | B |
| AZT | A | A | A | A | A | A | A | B |

Table legend:

$EC_{50}$: Concentration of compound required to achieve 50% protection of MT-4 cells against HIV-1-induced cytopathicity. A is <10 nM; B is 10-100 nM; C is >100 nM.

3. Conclusion

As indicated from the anti-HIV results, the invented tetrahydrothiopyranopyrimidine derivatives possessed a novel scaffold and excellent antiviral activities. Inhibitory activity of these compounds was less than 1 μM against both wide-type and mutant HIV-1, among which IA-1-4 demonstrated the best activity. Activity against wide-type HIV-1 of IA-1-4 was 30 folds better than NVP and comparable with second generation NNRTIs RPV. When it came to mutant HIV-1 strains, IIA-1-3 showed the best performance and indicated comparable activity against K103N and Y188L with ETV, and 2-fold more potent against L100I, Y181C and double mutant strains (F227L/V106A and Y181C/K103N) than ETV. Therefore, tetrahydrothiopyranopyrimidine derivatives were potent NNRTIs and can be further developed as anti-HIV agents.

The invention claimed is:

1. A compound of tetrahydrothiopyranopyrimidine, or pharmaceutically acceptable salt thereof, the compound having a general formula I or II shown as following:

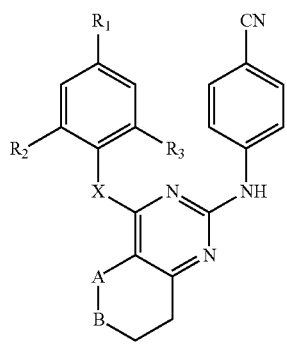

I

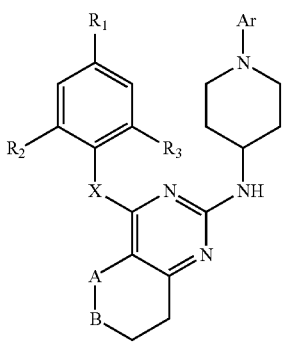

II wherein
A is $S(=O)_n$ or $CH_2$; B is $S(=O)_n$ or $CH_2$, while either A or B is $S(=O)_n$ in the compound; n=0, 1 or 2;
X is O or NH;
$R^1$, $R^2$ and $R^3$ are independently selected from a group consisting of H, halo, CN, $CF_3$, $NH_2$, OH, $C_{1-6}$alkyl, $C_{1-6}$alkyloxy, $C_{2-6}$alkenyl, trifluoromethyl, amino, hydroxy, cyanovinyl, cyanoethyl and cyclopropyl;
Ar is selected from a group consisting of an optionally substituted benzyl ring, an optionally substituted benzene ring, an optionally substituted naphthalene ring, a substituted 6-membered heterocyclic ring, a substituted 5-membered heterocyclic ring, a substituted 6-membered and 5-membered heterocyclic ring, a substituted 6- and 6-membered heterocyclic ring, a substituted five-membered and five-membered heterocyclic ring, a substituted benzo five-membered heterocyclic ring and a substituted benzo-six-membered heterocyclic ring.

2. The compound of claim 1, wherein $R^1$ and $R^3$ are $CH_3$, $R^2$ is selected from a group consisting of CN, Me and CH=CHCN.

3. The compound of claim 1, wherein the Ar has a general formula (a) or (b) shown as following:

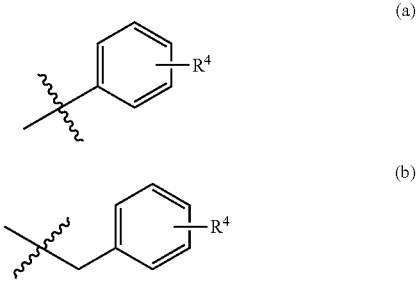

wherein $R^4$ is selected from a group consisting of H, CN, Me, $COR^5$, $COOR^5$, $CONH_2$, $CONHR^5$, $SO_2R^5$, $SO_2NH_2$, $SO_2NHR^5$, $NO_2$, $NH_2$, $NHR^5$, $NHCOR^5$ and $NHSO_2R^5$; $R^5$ is selected from a group consisting of $C_{1-10}$alkyl, $C_{1-10}$cyclicalkyl, $C_{1-10}$haloalkyl, $C_{1-10}$alkenyl and $C_{1-10}$aromatic alkyl.

4. The compound of claim 3, wherein the $R^5$ is Me or $CH_3CO$.

5. The compound of claim 3, wherein the compound have a formula (IA-1), (IA-2), (IB-1), (IB-2), (IIA-1), (IIA-2), (IIB-1), (IIB-2), (IIC-1), (IIC-2), (IID-1) or (IID-2) shown as following:

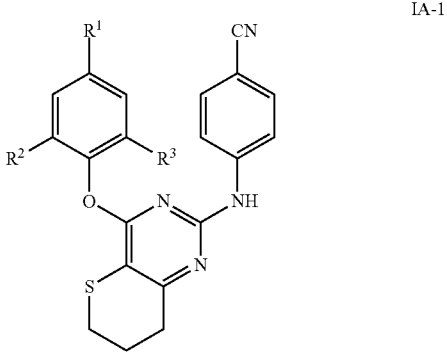

IA-1

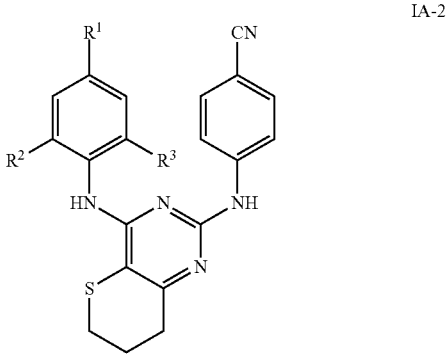

IA-2

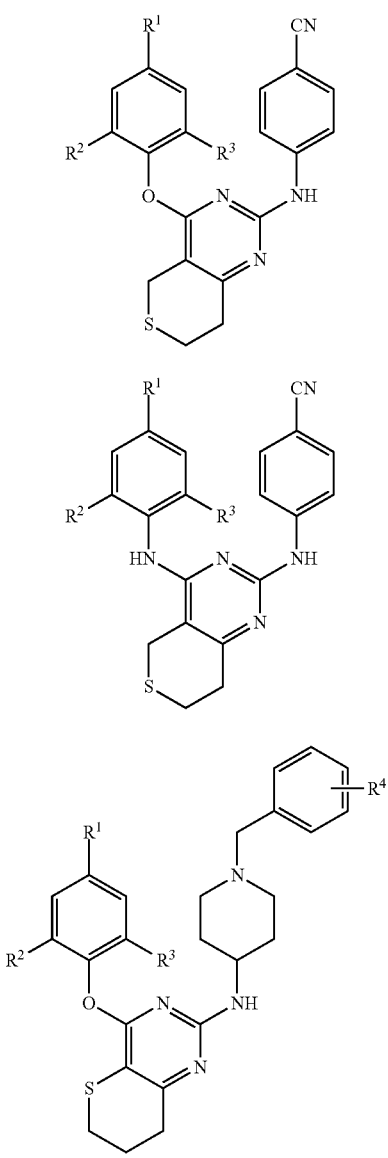
IB-1
IB-2
IIA-1
IIA-2
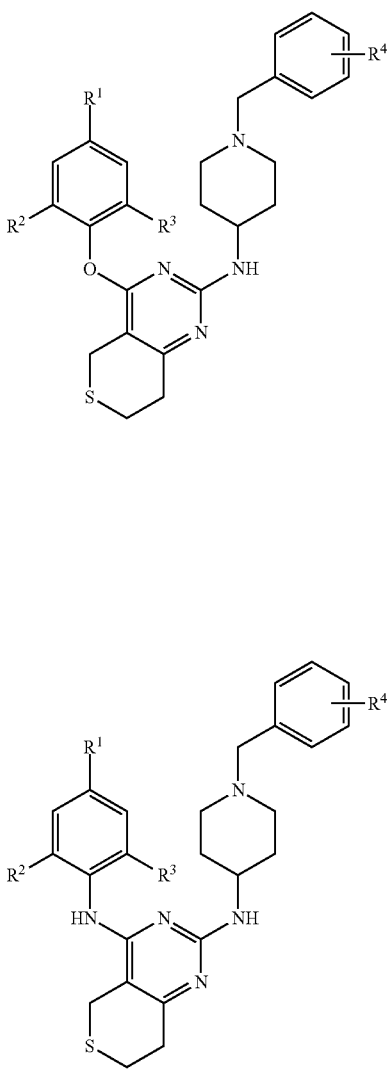
IIB-1
IIB-2
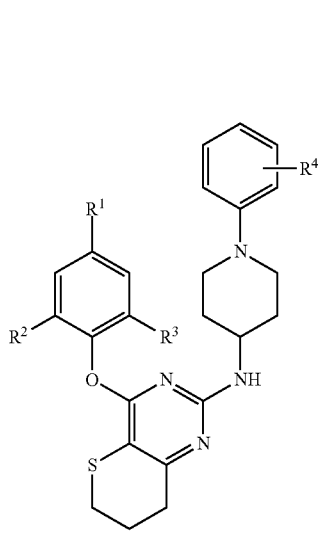
IIC-1

IIC-2
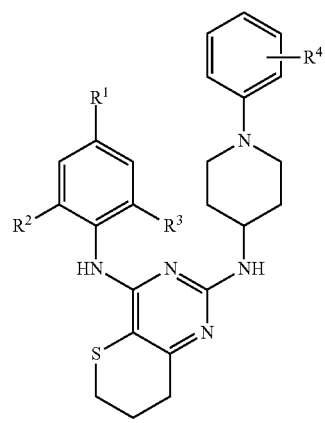
IID-1
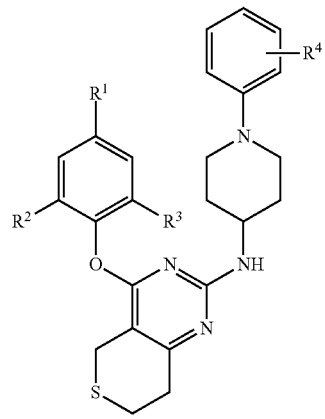
IID-2
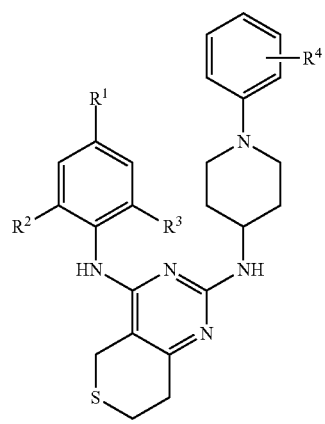
wherein, $R^1$, $R^2$, $R^3$, $R^4$ are independently selected from a group consisting of H, halo, CN, $CF_3$, $NH_2$, OH, $C_{1-6}$alkyl, $C_{1-6}$ alkyloxy, $C_{2-6}$alkenyl, trifluoromethyl, amino, hydroxy, cyanovinyl, cyanoethyl and cyclopropyl.
6. The compound of claim 5, the compound is selected from a group consisting of
IA-1-1
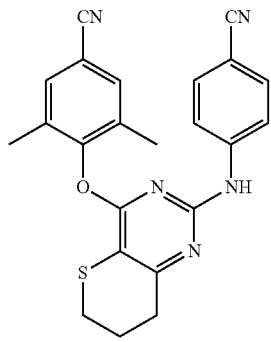
IA-1-2
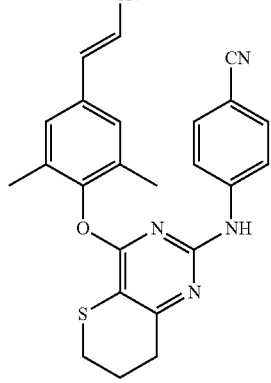
IA-1-3
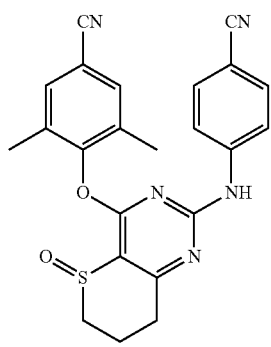
IA-1-4

IIA-1-1
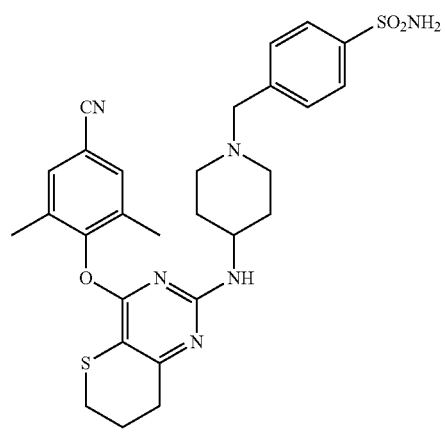
IIA-1-2
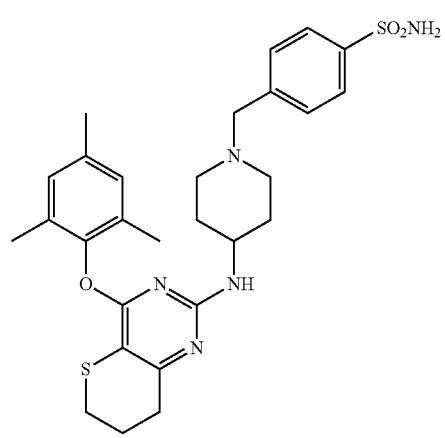
IIA-1-3
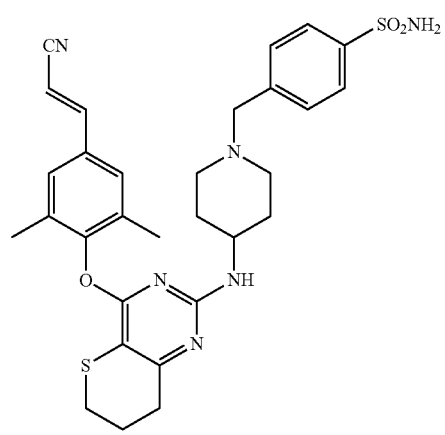
IIA-1-4
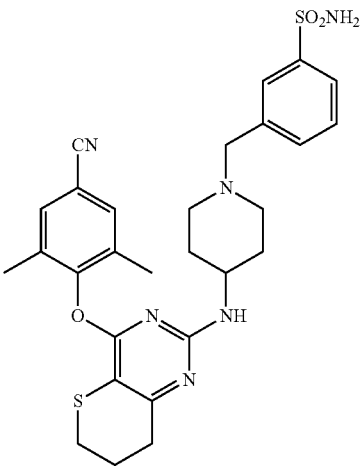
IIA-1-5
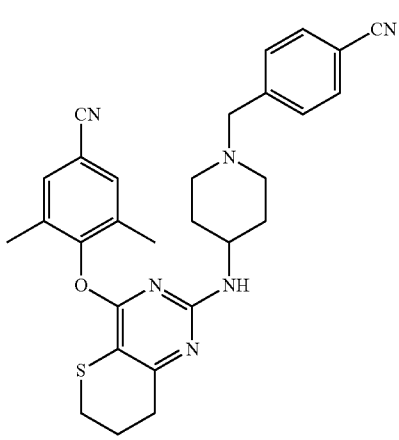
IIA-1-6
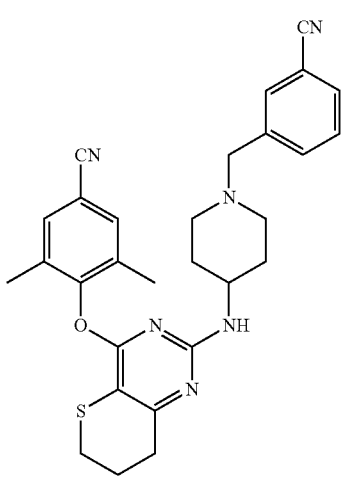

IIA-1-7
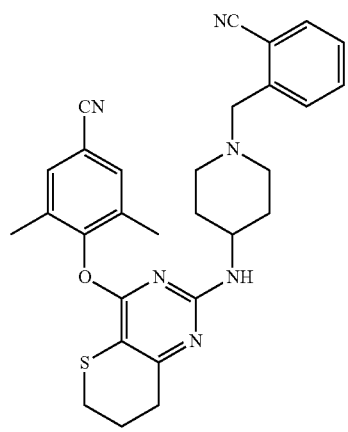
IIA-1-10
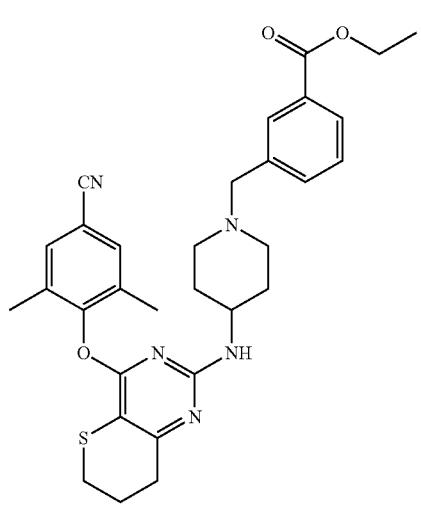
IIA-1-8
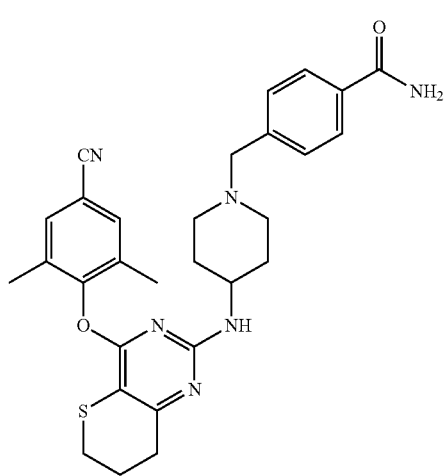
IIA-1-11
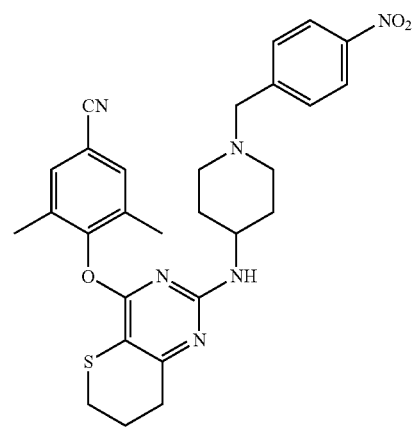
IIA-1-9
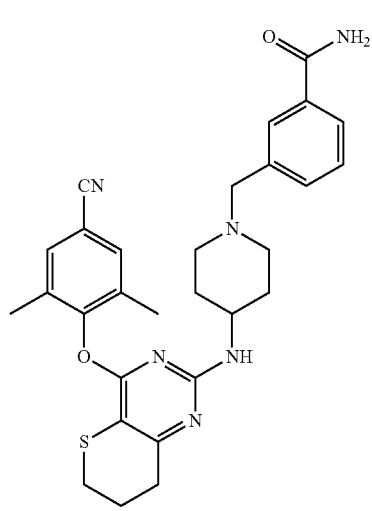
IIA-1-12
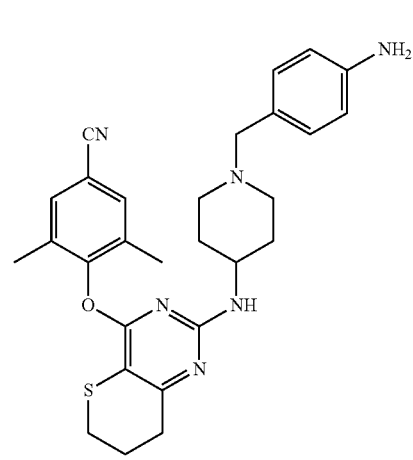

-continued

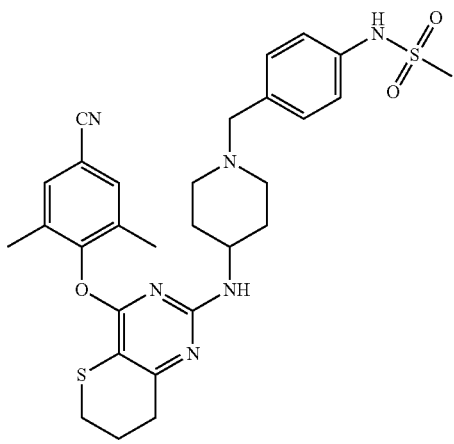

IIA-1-13

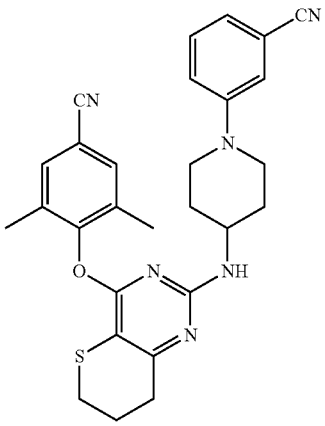

IIC-1-2

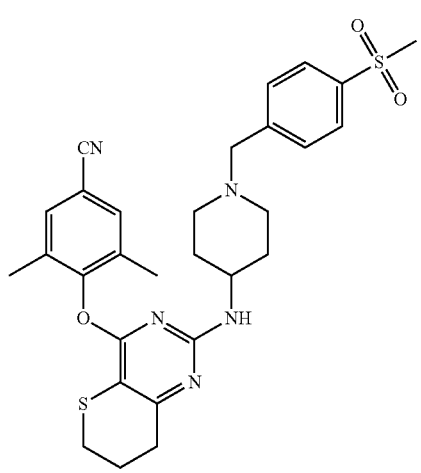

IIA-1-14

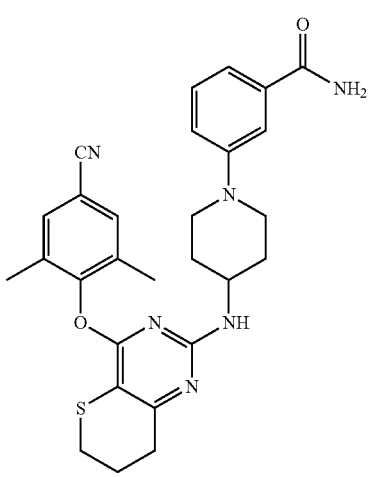

IIC-1-1

-continued

IIC-2-1

7. The compound of claim 1, wherein the compound is prepared by the following steps:

methyl mercaptoacetate (A) reacting with methyl 4-chlorobutanoate (B) to give methyl 4-((2-methoxy-2-oxoethyl) thio) butyrate (C) in sodium methoxide; the intermediate C being converted to oxotetrahydropyranyl ester (D) by Dieckmann condensation under sodium methoxide; the intermediate D being cyclized with methyl isothiourea into 2-methylmercaptothiopyranopyrimidine-2-ol (E) in potassium hydroxide; the intermediate E being hydrolyzed into tetrahydrothiopyrano pyrimidine-2,4-diol (F) in acetic acid; the intermediate F being base chlorinated with N, N-dimethylaniline into 2,4-dichloro tetrahydrothiopyranopyrimidine (G) in phosphorus oxychloride; the intermediate G being reacted by substituting phenol or aniline to give an intermediate H under alkaline condition; the intermediate H being reacted with the corresponding substituted aniline to obtain a final compound; or the intermediate H being reacted with 1-boc-4-aminopiperidine, deprotected with boc, then reacted with corresponding benzyl chloride or benzyl bromide to obtain the final compound; above reactions shown as the

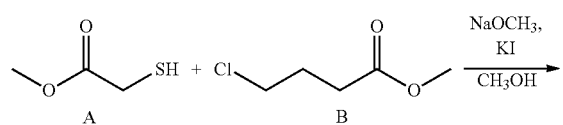

A      B

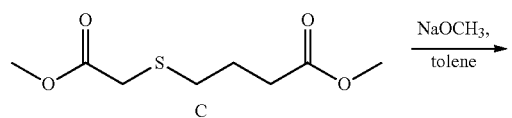

C

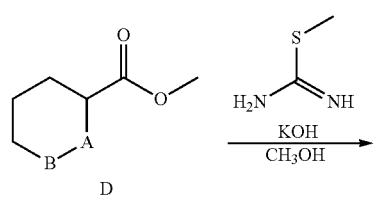

D

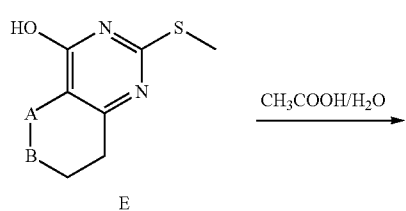

E

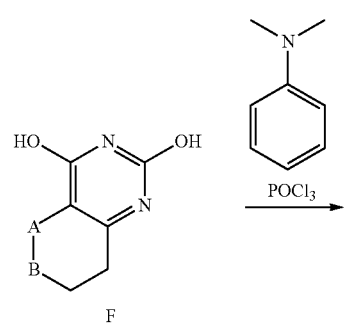

F

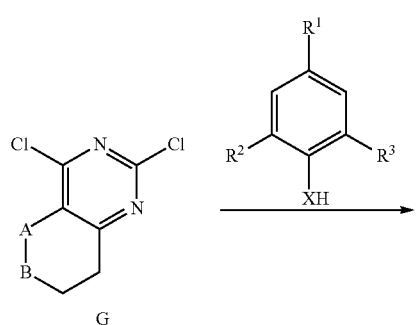

G

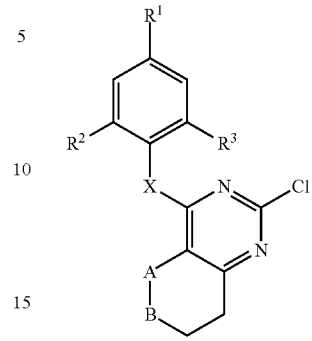

H

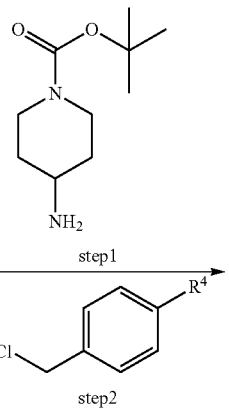

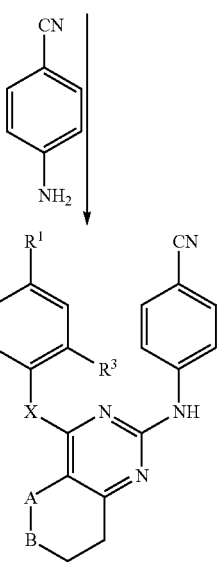

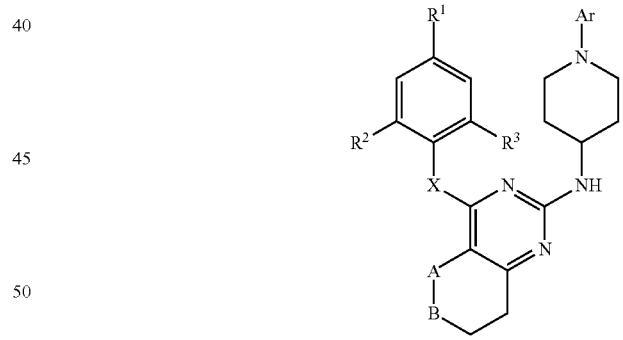

following:

wherein reagents and conditions are (i) sodium methoxide, potassium iodide, methanol, reflux; (ii) sodium methoxide, toluene, 105° C.; (iii) methylisothiourea sulfate, potassium hydroxide, (V) phosphorus oxychloride, N, N-dimethylaniline at 90° C.; (vi) potassium carbonate, N, N-dimethylformamide, substituted phenol or aniline; 1-Boc-4-aminopiperidine, N, N-diisopropylethylamine, N-methylpyrrolidone at 120-130° C.; b) trifluoroacetic acid in dichloromethane at room temperature; c) (Viii) 1-Substituted-4-aminopiperidine, N, N-diisopropylethylamine, N-methylpyrrolidone, 130° C.; (ix) 4-aminobenzonitrile, 2,2'-bis-(diphenylphosphino)-1,1'-binaphthyl, tris (dibenzylideneacetone) dipalladium, dioxane;

wherein, the 2,4,6-trisubstituted phenol/aniline is selected from a group consisting of 2,4,6-trimethylphenol, 4-hydroxy-3,5-dimethylbenzonitrile, (E)-3-(4-hydroxy-3,5-dimethylphenyl)acrylonitrile, 2,4,6-trimethylaniline, 4-amino-3,5-dimethylbenzonitrile, and (E)-3-(4-amino-3,5-dimethylphenyl)acrylonitrile;

wherein, the substituted benzyl chloride/bromide is selected from a group consisting of 1-chloro-2-(chloromethyl)benzene, 1-chloro-3-(chloromethyl)benzene, 1-chloro-4-(chloromethyl)benzene, 1-bromo-2-(bromomethyl)benzene, 1-bromo-3-(bromomethyl)benzene, 1-bromo-4-(bromomethyl)benzene, 1-(chloromethyl)-2-fluorobenzene, 1-(chloromethyl)-3-fluorobenzene, 1-(chloromethyl)-4-fluorobenzene, 1-(bromomethyl)-2,4-difluorobenzene, 1-(bromomethyl)-3,4-difluorobenzene, 2-(chloromethyl)benzonitrile, 3-(chloromethyl)benzonitrile, 4-(chloromethyl)benzonitrile, 1-(cholomethyl)-2-nitrobenzene, 1-(chloromethyl)-3-nitrobenzene, 1-(chloromethyl)-4-nitrobenzene, 1-(chloromethyl)-2-methoxybenzene, 1-(chloromethyl)-3-methoxybenzene, 1-(chloromethyl)-4-methoxybenzene, 1-(bromomethyl)-4-(methylsulfonyl)benzene, 4-(bromomethyl)benzenesulfonamide, 3-(bromomethyl)benzenesulfonamide, 2-(bromomethyl)benzamide, N-(4-(bromomethyl)phenyl)formamide, ethyl 4-(bromomethyl)benzoate, 4-(bromomethyl)benzamide, 3-(bromomethyl)benzamide and N-(4-(bromomethyl)phenyl)methanesulfonamide;

wherein

A is $S(=O)_n$ or $CH_2$; B is $S(=O)_n$ or $CH_2$, while either A or B is $S(=O)_n$ in one compound; n=0, 1 or 2;

X is O or NH;

$R^1$, $R^2$ and $R^3$ are independently selected from a group consisting of H, halo, CN, $CF_3$, $NH_2$, OH, $C_{1-6}$alkyl, $C_{1-6}$alkyloxy, $C_{2-6}$alkenyl, trifluoromethyl, amino, hydroxy, cyanovinyl, cyanoethyl and cyclopropyl.

8. A method for preventing HIV infection or treating HIV-infected patient comprising a step of administrating to a subject in need a therapeutically effective amount of the compound of claim 1 or its pharmaceutically acceptable salt.

9. A pharmaceutical composition comprising a therapeutically effective amount of the compound of claim 1 or its pharmaceutically acceptable salt and one or more pharmaceutical acceptable carrier or excipient.

* * * * *